(12) United States Patent
Yarger et al.

(10) Patent No.: US 9,422,324 B2
(45) Date of Patent: Aug. 23, 2016

(54) 6-SUBSTITUTED DEMETHYL-ESTRADIOL DERIVATIVES AS SELECTIVE ER-β AGONISTS

(71) Applicant: Endece, LLC, Mequon, WI (US)

(72) Inventors: James G. Yarger, Cedarburg, WI (US); Steven H. Nye, Mequon, WI (US)

(73) Assignee: Endece LLC, Mequon, WI (US)

( * ) Notice: Subject to any disclaimer, the term of this patent is extended or adjusted under 35 U.S.C. 154(b) by 40 days.

(21) Appl. No.: 14/320,110

(22) Filed: Jun. 30, 2014

(65) Prior Publication Data

US 2014/0315874 A1    Oct. 23, 2014

Related U.S. Application Data

(62) Division of application No. 13/232,798, filed on Sep. 14, 2011, now abandoned.

(60) Provisional application No. 61/382,752, filed on Sep. 14, 2010.

(51) Int. Cl.
| | | |
|---|---|---|
| A61K 31/56 | (2006.01) | |
| C07J 1/00 | (2006.01) | |
| C07J 31/00 | (2006.01) | |
| C07J 41/00 | (2006.01) | |
| C07J 17/00 | (2006.01) | |
| C07J 51/00 | (2006.01) | |

(52) U.S. Cl.
CPC ............... C07J 1/007 (2013.01); A61K 31/56 (2013.01); C07J 1/0059 (2013.01); C07J 31/006 (2013.01); C07J 41/0016 (2013.01); C07J 41/0044 (2013.01); C07J 1/0074 (2013.01); C07J 17/00 (2013.01); C07J 51/00 (2013.01)

(58) Field of Classification Search
CPC ...................................................... A61K 31/56
See application file for complete search history.

(56) References Cited

U.S. PATENT DOCUMENTS

| | | |
|---|---|---|
| 3,274,176 A | 9/1966 | Dube |
| 3,377,363 A | 4/1968 | Tadanier |
| 4,732,904 A | 3/1988 | Morgan |
| 4,808,616 A | 2/1989 | Buzzetti et al. |
| 4,876,045 A | 10/1989 | Longo et al. |
| 4,904,650 A | 2/1990 | Buzzetti et al. |
| 4,990,635 A | 2/1991 | Longo et al. |
| 5,892,069 A | 4/1999 | D'Amato et al. |
| 5,914,324 A | 6/1999 | De Munari et al. |
| 6,384,250 B2 | 5/2002 | Gobbini et al. |
| 6,958,327 B1 | 10/2005 | Hillisch et al. |
| 7,846,918 B2 | 12/2010 | Pariza et al. |
| 2003/0055029 A1 | 3/2003 | D'Amato et al. |
| 2005/0192263 A1 | 9/2005 | Messinger et al. |
| 2006/0009434 A1 | 1/2006 | Hillisch et al. |
| 2008/0119447 A1 | 5/2008 | Yarger |
| 2008/0234505 A1 | 9/2008 | Kunnen et al. |
| 2008/0312202 A1 | 12/2008 | Yarger |
| 2009/0105198 A1 | 4/2009 | Hill et al. |
| 2010/0130463 A1 | 5/2010 | Yarger |
| 2010/0197647 A1 | 8/2010 | Reed et al. |

FOREIGN PATENT DOCUMENTS

| | | |
|---|---|---|
| CN | 101594874 A | 2/2009 |
| DE | 258820 | 8/1988 |
| JP | 2003513102 | 4/2008 |
| JP | 2013512260 | 4/2011 |
| WO | 2005070951 A1 | 8/2005 |
| WO | 2008067450 A2 | 6/2008 |

OTHER PUBLICATIONS

U.S. Appl. No. 13/232,798, filed Sep. 14, 2011.
Shenghong Xu et al. "17 Beta-Estradiol Activates Estrogen Receptor Beta-Signalling and Inhibits Transient Receptor Potential Vanilloid Receptor 1 Activation by Capsaicin in Adult Rat Nociceptor Neurons", Endocrinology, vol. 149 (11), 2008, 5540-5548.
Supplementary European Search Report for EP 11825878 issued Aug. 28, 2014, 9 pages.
Written Opinion of the International Searching Authority from PCT/US2011/051608, issued Apr. 19, 2012, 8 pages.
Spooner M. F. et al., "Endogenous Pain Modulation During the Formalin Test in Estrogen Receptor Beta Knockout Mice", Neuroscience, 2007, vol. 150, p. 675-80.

*Primary Examiner* — Noble Jarrell
*Assistant Examiner* — John S Kenyon
(74) *Attorney, Agent, or Firm* — Reinhart Boerner Van Deuren s.c.

(57) ABSTRACT

Disclosed herein are 6-substituted 13-demethyl-estradiol derivatives as selective ERβ agonists. Also disclosed is a method for treating pain by administering these 6-substituted 13-demethyl-estradiol derivatives.

22 Claims, 3 Drawing Sheets

6-SUBSTITUTED DEMETHYL-ESTRADIOL DERIVATIVES AS SELECTIVE ER-β AGONISTS

This application is a divisional of and claims priority to and the benefit of application Ser. No. 13/232,798 filed Sep. 14, 2011, which claims priority from U.S. Provisional Patent Application Ser. No. 61/382,752 filed on Sep. 14, 2010, the disclosure of each of which is incorporated herein by reference in its entirety.

FIELD OF THE INVENTION

The present invention relates to compositions and methods of making and using 6-substituted 13-demethyl-estradiol compounds and their pharmaceutically acceptable salts or prodrugs thereof as articulated and described herein. The compounds have been unexpectedly found to be useful as ERβ specific agonists, possessing virtually no functional activity with ERα. As such, the present invention also pertains to pharmaceutical compositions comprising such compounds, present either in vitro or in vivo, for both diagnostic applications and also treatment of neuropathic pain.

BACKGROUND OF THE INVENTION

Research on the function and activity of estrogen receptors, the structure and their function has been the subject of many recent investigations. Estrogen receptors belong to a large family of structurally related ligand-inducible transcription factors, including steroid receptors, thyroid/retinoid receptors, vitamin D receptors known as nuclear receptors. While the true ligand for nuclear receptors have not been described, there are distinct small molecules that are able to bind to such receptors and trigger a cellular response.

Estrogens and estrogen receptor modulators bind to estrogen receptors, classified into two types; α and β, to form discrete molecular complexes that exert pleiotropic tissue-specific effects by modulating the expression of target genes. The ligand-bound estrogen receptor acts as a key transcription factor in various molecular pathways, and modulation of ER expression levels is important in determining cellular growth potential.

While both these types of receptors bind to estrogen, as well as other agonists and antagonists, the two receptors have distinctly different localization concentration within the body. Aside from some structural differences between the α and β types, when complex with estrogen, the two are shown to signal in opposite ways, with estrogen activating transcription in the presence of Estrogen Receptor α (ERα) and inhibiting transcription in the presence of Estrogen Receptor β (ERβ).

Estrogens regulate a large spectrum of neuronal functions, including pain perception. Recently, hotplate and formalin tests carried out in wild type (WT) and ERβ knockout (KO) mice demonstrated that pain inhibitory mechanisms and early tonic pain are modified by ERβ deficiency. Spooner, M. F. et al., *Neuroscience* 150, 675-680 (2007). Spooner et al. found that nociceptive responses are lower in ERβ KO female than in WT female mice during the interphase and early tonic phase II of the formalin test but not during acute and late tonic phases. This suggests that estrogen, through its actions on ERβ, dampens the efficacy of endogenous pain modulation mechanisms during the interphase and/or inflammation prosedd in the early phase II, triggering an increase in spinal nociceptive neuronal activity.

Further, ERb-131, a non-steroidal ERβ ligand was evaluated in several pain animal models involving nerve injury or sensitization. Piu, F. et al., *European Journal of Pharmacology* 590, 423-429 (2008); Piu, F. et al., *European Journal of Pharmacology* 592, 158-159 (2008). Using functional and binding assays, ERb-131 was characterized as a potent and selective ERβ agonist. In vivo, ERb-131 was devoid of estrogen receptor alpha activity as assessed in a rat uterotrophic assay. Also, ERb-131 alleviated tactile hyperalgesia induced by capsaicin, and reversed tactile allodynia caused by spinal nerve ligation and various chemical insults. Moreover, ERb-131 did not influence the pain threshold of normal healthy animals. In the chronic complete Freund's adjuvant model, ERb-131 resolved both inflammatory and hyperalgesic components of chronic pain. Thus, Piu et al. also demonstrates that ERβ agonism is a critical effector in attenuating a broad range of anti-nociceptive states.

Accordingly, there exists a need for new compounds that can selectively act on ERβ to assist in the treatment of pain. To date, none of the teachings of the prior art provide for a therapeutic 6-substituted 13-demethyl estradiol derivative that can be used for this type of treatment.

SUMMARY OF THE INVENTION

In light of the foregoing, the present invention is directed towards analgesic compounds, compositions and methods for their use and preparation, thereby overcoming various deficiencies and shortcomings of the prior art, including those outlined above. Accordingly, it is one object of the present invention to provide compounds useful in the treatment of estrogen-dependent conditions.

Another object of the present invention is to provide compounds and methods for the treatment of pain with compounds that selectively act on ERβ. The compounds can be selective agonists or antagonists of ERβ.

The present invention includes compounds represented in Formula I.

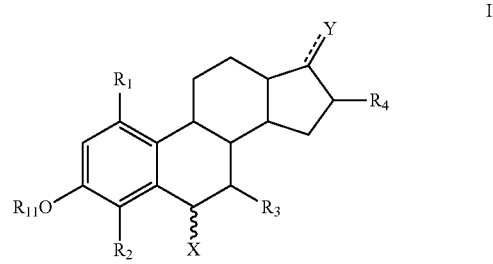

wherein $R_1$, $R_2$, $R_3$ and $R_4$ are independently hydrogen, $C_1$-$C_6$ alkyl, halo, a sulfate, a glucuronide, —OH, a bulky group, aryl, cycloalkyl, heteroaryl, heterocycloalkyl, —N(CH$_2$)$_n$; a phosphate group, and a phosphinate group; $R_{11}$ is selected from the group consisting of H, $C_1$-$C_6$ alkyl, halogen, a sulfate, a glucuronide, —SO$_2$NH$_2$, —COOH, —CN, —CH$_2$CN—, —NHCN—, —CHO, =CHOCH$_3$, —COO salt, —OSO$_2$alkyl, —NH$_2$, and —NHCO(CH$_2$)$_n$; X is selected from the group consisting of hydrogen, $C_1$-$C_{12}$ alkyl, $C_2$-$C_{12}$ alkenyl, $C_2$-$C_{12}$ alkynyl, halogen, a glucuronide, —NH$_2$, —SO$_2$NH$_2$, —COOH, —CN, —CH$_2$CN, —NHCN, —CHO, —COO salt, —OSO$_2$alkyl, —SH, —SCH$_3$, —CH[(CH$_2$)$_n$CH$_3$]COOCH$_3$, —(CH$_2$)$_m$COOCH$_3$, —(CH$_2$)$_m$—O—CH$_3$, —(CH$_2$)$_m$—O—(CH$_2$)$_n$CH$_3$, —(CH$_2$)$_m$—S—CH$_3$, —(CH$_2$)$_m$—S—(CH$_2$)$_n$CH$_3$, —(CH$_2$)$_m$—NH—(CH$_2$)$_n$CH$_3$, —$C_2$-$C_8$ alkenyl-O—$(CH_2)_n CH_3$, —$C_2$-$C_8$ alkenyl-S—$(CH_2)_n CH_3$, —$C_2$-$C_8$ alkenyl-N—$(CH_2)_n CH_3$, —$C_2$-$C_8$ alkynyl-O—$(CH_2)_n CH_3$, —$C_2$-$C_8$ alkynyl-S—$(CH_2)_n CH_3$, —$C_2$-$C_8$ alkynyl-N—$(CH_2)_n CH_3$, —$(CH_2)_m$—OH, —$(CH_2)_m$—$NH_2$, —$(CH_2)_m$—O—$NH_2$, —$(CH_2)_m$—S—$NH_2$, —$NH(CH_2)_m CH_3$, —$NH(CH_2)_m OCH_3$, —$NH(CH_2)_m CHOH$—COOH, —$N(CH_3)_2$, —$(CH_2)_m(NH)CH_2 OH$, —NHCOOH, —$(CH_2)_m NHCOOH$, —$NO_2$, —SCN, —$SO_2$alkyl, —$B(OH)_2$, —$(CH_2)_m N(CH_3)$—$SO_2$—$NH_3$, —$(CH_2)_m$—NH—$SO_2$—$NH_2$, —NHC(=S)$CH_3$, and —$NHNH_2$; and Y is selected from hydrogen, =O, —OCO($R_6$) and —OH; wherein m is an integer between 0-20, n is an integer between 0-8, the === symbol represents either a single or a double bond capable of forming a keto group at position 3 or 17; and the ~~ symbol represents any type of bond regardless of the stereochemistry; and the respective enantiomers, other stereochemical isomers, hydrates, solvates, tautomers and pharmaceutically acceptable salts of said compounds.

Specific examples of compounds of Formula I are shown below:

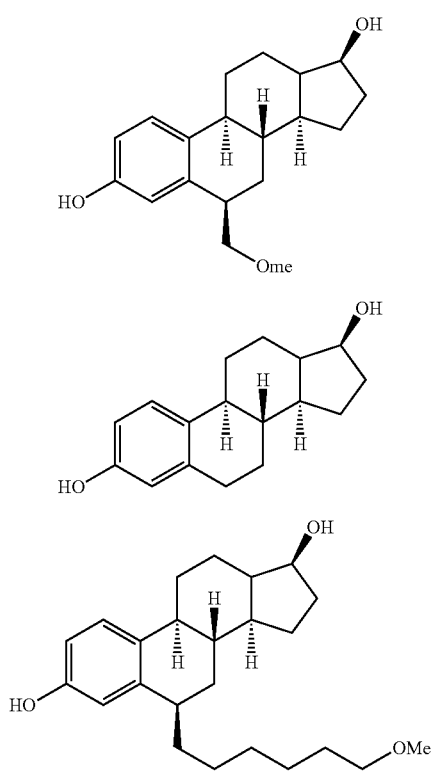

At least another aspect of the invention concerns delivery systems that allows conversion of suitable analogues which can be converted to a specified active compound in vivo after it is administered to the patient for exerting its therapeutic activity.

The compounds of the present invention may also be used in combination-based therapeutic pain treatments in a mammalian subject. Such methods may comprise administration of a compound of Formula I in combination with other adjunct pain therapies as known in the art.

Any of the compounds of the present invention may be contemplated for administration to the mammalian subject in the form of a drug, prodrug or even active metabolite. In the methods of treatment of the present invention, the term "administering" shall encompass the treatment of the various conditions described with the compound specifically disclosed or with a compound which may not be specifically disclosed, but which converts to the specified compound in vivo after administration to the patient and exhibits therapeutic activity.

Other objects, features, benefits and advantages of the present invention will be apparent from this summary and the following descriptions of certain embodiments, and will be readily apparent to those skilled in the art having knowledge of various chemotherapeutic compounds, methods and/or modes of operation.

DETAILED DESCRIPTION OF THE INVENTION

Figure 1:
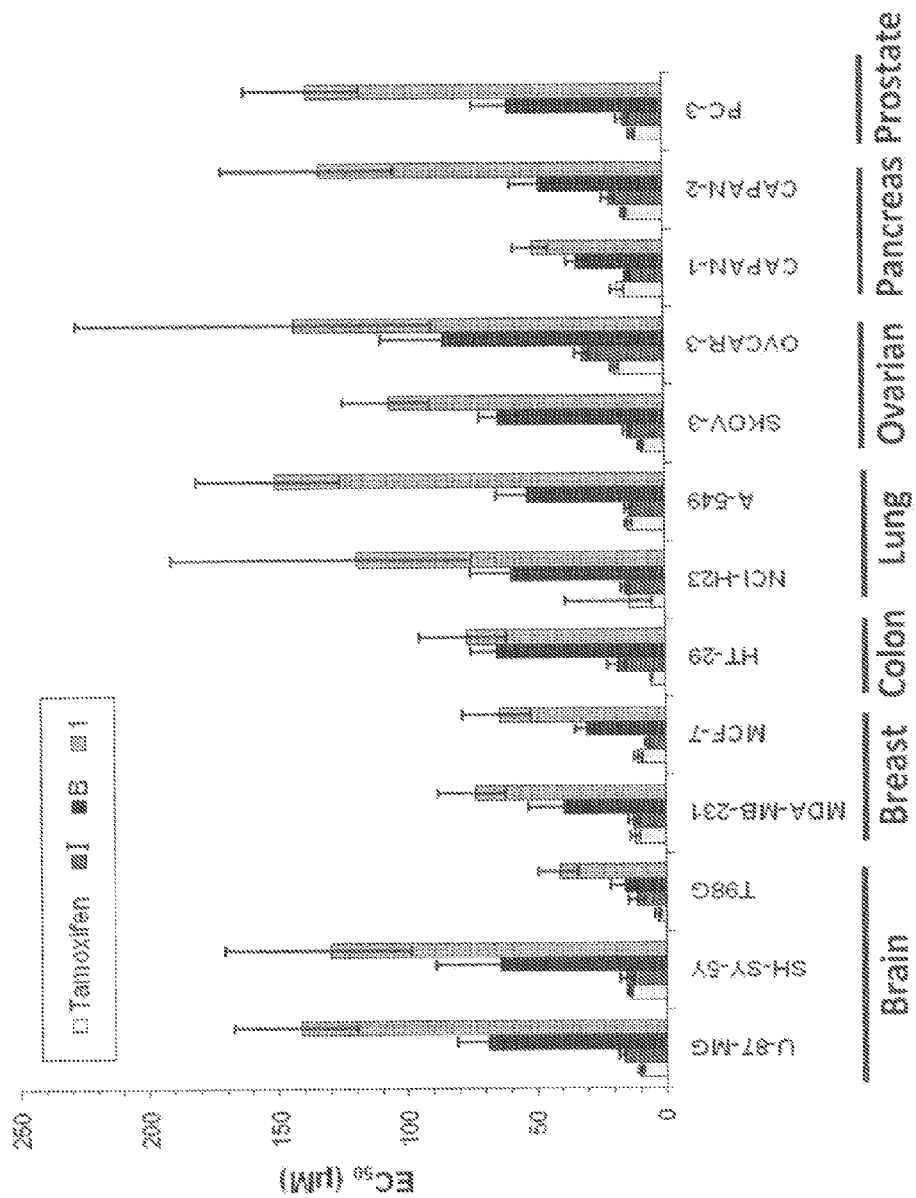
FIG. 1 is a graph of the $EC_{50}$ values of compounds B, I and 1, and Tamoxifen in various cell lines for compounds of the invention.

Unless defined otherwise, all technical and scientific terms used herein have the same meaning as is commonly understood by one of skill in the art to which this invention belongs and shall be understood to have the meanings described below. All publications and patents referred to herein are incorporated by reference in their entirety. Unless otherwise specified, a reference to a particular compound includes all such isomeric forms, including racemic and other mixtures thereof. Unless otherwise specified, a reference to a particular compound also includes ionic, salt, solvate (e.g., hydrate), protected forms, prodrugs, and other stereoisomers thereof, for example, as discussed herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19, and discussed herein.

Compounds of the present invention have application in the treatment of pain, and so the present invention further provides anti-nociceptive agents, or analgesics. The term "anti-nociceptive agent" as used herein, pertains to a compound which treats, delays, reduces and/or increases the tolerance of, pain. The analgesic effect may arise through one or more mechanisms, or any combination thereof.

The invention further provides active compounds for use in a method of treatment of the human or animal body by therapy. Such a method may comprise administering to such a subject a therapeutically-effective amount of an active compound, preferably in the form of a pharmaceutical composition as discussed further herein.

The term "estrogen" as used herein encompass steroid like hormones that are naturally made and is able to cross the cell membrane to exert its activity inside the cell by binding to the estrogen receptors. Example of such compounds include but are not limited to estradiols, estrols, and esterenes.

The term "treatment," or "therapy" as used herein in the context of treating a condition, pertains generally to treatment and therapy of a mammalian subject, whether of a human or a non-human animal (e.g., in veterinary applications), in which some desired therapeutic effect is achieved, for example, the inhibition of the progress of the condition, and includes a reduction in the rate of progress, a halt in the rate of progress, amelioration of the condition, and/or cure of the condition. Treatment as a prophylactic measure is also included. Treatment includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., employing protecting groups including phosphoric acid derivatives and phosphinates at suitable positions such as position 3 or 17, other compounds used for photodynamic therapy, GDEPT, ADEPT, etc.); surgery; radiation therapy; gene therapy; and other analgesics.

The term "stereochemical isomer" as used herein, refers to isomers that differ from each other only in the way the atoms are oriented in space. The two stereoisomers particularly of importance in the instant invention are enantiomers and diastereomers depending on whether or not the two isomers are mirror images of each other. In the preferred embodiment, the claimed formulations comprise such compounds that isolated, resolved and are "substantially free of other isomers."

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "patient" refers to animals, including mammals, preferably humans.

The term "region of a patient" refers to a particular area or portion of the patient afflicted with pain, and in some instances to regions throughout the entire patient. Exemplary of such regions are the pulmonary region, the gastrointestinal region, the breast region, the renal region as well as other bodily regions, tissues, lymphocytes, receptors, organs and the like, including the vasculature and circulatory system, and cancerous tissue. "Region of a patient" includes, for example, regions to be treated with the disclosed compounds and compositions. The "region of a patient" can be internal or external.

The term "tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include breast tissue, including breast cells, membranous tissues, including endothelium and epithelium, laminae, connective tissue, including interstitial tissue, and tumors.

By "alkyl" in the present invention is meant a straight or branched chain alkyl radical having 1-20, and preferably from 1-12, carbon atoms. Examples include but are not limited to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as, for example, a halo, hydroxyl, cycloalkyl, aryl, alkenyl or alkoxy group and the like.

By "aryl" is meant an aromatic carbocylic radical having a single ring (e.g. phenyl), multiple rings (e.g. biphenyl) or multiple fused rings in which at least one is aromatic (e.g. 1,2,3,4-tetrahydronaphthyl). The aryl group can also be optionally mono-, di-, or trisubstituted with, for example, halo, hydroxyl, alkyl, alkenyl, cycloalkyl or alkoxy and the like.

By "heteroaryl" is meant one or multiple fused aromatic ring systems of 5-, 6- or 7-membered rings containing at least one and up to four heteroatoms selected from nitrogen, oxygen or sulfur. Examples include but are not limited to furanyl, thienyl, pyridinyl, pyrimidinyl, benzimidazolyl and benzoxazolyl. The heteroaryl group can also be optionally mono-, di-, or trisubstituted with, for example, halo, hydroxyl, alkyl, alkenyl, cycloalkyl or alkoxy and the like.

By "cycloalkyl" is meant a carbocylic radical having a single ring (e.g. cyclohexyl), multiple rings (e.g. bicyclohexyl) or multiple fused rings (e.g.). The cycloalkyl group can optionally contain from 1 to 4 heteroatoms. In addition, the cycloalkyl group may have one or more double bonds. The cycloalkyl group can also be optionally mono-, di-, or trisubstituted with, for example, halo, hydroxyl, alkyl, alkenyl, aryl or alkoxy and the like.

By "alkoxy" is meant an oxy-containing radical having an alkyl portion. Examples include, but are not limited to, methoxy, ethoxy, propoxy, butoxy and tert-butoxy. The alkoxy group can also be optionally mono-, di-, or trisubstituted with, for example, halo, hydroxyl, aryl, cycloalkyl or alkoxy and the like.

By "alkenyl" is meant a straight or branched hydrocarbon radical having from 2 to 20, and preferably from 2-6, carbon atoms and from one to three double bonds and includes, for example, ethenyl, propenyl, 1-but-3-enyl, 1-pent-3-enyl, 1-hex-5-enyl. The alkenyl group can also be optionally mono-, di-, or trisubstituted with, for example, halo, hydroxyl, aryl, cycloalkyl or alkoxy and the like.

"Halo" or "halogen" is a halogen radical of fluorine, chlorine, bromine or iodine.

By "glucuronide" is meant a glycoside radical of glucuronic acid.

The term "sulfate" refers to a radical having the general formula —OS(O)$_2$—OR', wherein R' is hydrogen, a metal or an alkyl group.

The term "phosphate" refers to a radical having the general formula —OP(O)(OR')$_2$, wherein each R' is independently hydrogen, a metal or an alkyl group.

The term "phosphinate" refers to a radical having the general formula —OP(O)(R')$_2$, wherein each R' is independently hydrogen, a metal or an alkyl group.

By "bulky group" is meant a substituent that produces steric hindrance about the space to which it is attached, e.g. a t-butyl group.

The term "amino alkyl" as used herein refers to an alkyl group with an amino group on it, for example, H$_2$N—CH$_2$—, H$_2$N—CH$_2$CH$_2$—, Me$_2$NCH$_2$—, etc., wherein the point of attachment is a carbon of the alkyl chain; and the term "alkyl amino" as used herein refers to an amino group with an alkyl group attached to the nitrogen atom, for example, CH$_3$NH—, EtNH—, iPr—NH—, etc., wherein the point of attachment is via the nitrogen atom of the amino group. All other terms wherein successive radicals are employed will adhere to a similar rule.

By "demethyl" is meant the absence of a methyl group.

The term "proliferative cell disorders" as used herein refers to disorders such as tumors, primary malignant tumors, and other hyperproliferative conditions. The terms "primary malignant tumor(s)" and "cancer(s)" are used interchangeably.

Compounds

Among other things, the present invention relates to 13-demethyl estradiol derivatives with specific modifications at C-6 on the B ring of the estradiol, and the lack of a methyl group at C-13 on the C ring. At least one aspect of this invention is directed to such compounds having the general structure of Formula I shown above.

In an embodiment of the present invention, preferred compounds have the general structure shown in Formula Ia below:

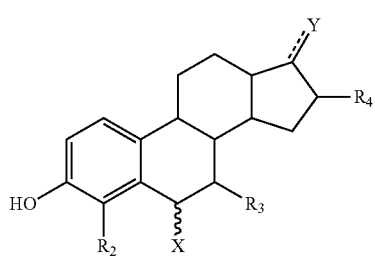

Ia wherein $R_2$, $R_3$, $R_4$, X and Y are as defined above for Formula I. Even more preferably, Y is selected from =O and —OH; $R_4$ is selected from hydrogen, halo and $C_1$-$C_6$ alkyl; $R_2$ is selected from hydrogen, —OH and halo; $R_3$ is selected from hydrogen, halo and —OH; and X is selected from $C_1$-$C_{12}$ alkyl, $C_2$-$C_{12}$ alkyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, —NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$ N(CH$_3$)—SO$_2$—NH$_3$, and —$(CH_2)_m$—NH—SO$_2$—NH$_2$; m is an integer from 1-20; n is an integer from 0-8; and the === symbol represents either a single or a double bond. Yet even more preferably, Y is (S)—OH; $R_4$ is selected from hydrogen or alkyl; $R_2$ is hydrogen; $R_3$ is hydrogen; and X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_n$CH$_3$; m is an integer from 1-12; n is an integer from 0-4.

Yet another embodiment of the present invention is directed to a chemotherapeutic compound of a Formula Ib:

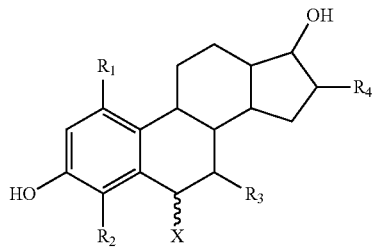

Ib wherein $R_1$ $R_2$, $R_3$, $R_4$ and X are as defined above for Formula I. Even more preferably, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, alkenyl-N—$(CH_2)_n$CH$_3$, —$C_2$-$C_8$ alkynyl-O—$(CH_2)_n$CH$_3$, alkynyl-S—$(CH_2)_n$CH$_3$, —$C_2$-$C_8$ alkynyl-N—$(CH_2)_n$CH$_3$—$(CH_2)_n$CH$_3$—$(CH_2)_m$—OH, —$(CH_2)_m$—O—NH$_2$, —$(CH_2)_m$—S—NH$_2$, —NH$(CH_2)_m$CH$_3$, —NH$(CH_2)_m$OCH$_3$, NH$(CH_2)_m$CHOH—COOH, —$(CH_2)_m$ (NH)CH$_2$OH, —$(CH_2)_m$NHCOOH, —$(CH_2)_m$N(CH$_3$)—SO$_2$—NH$_3$, and —$(CH_2)_m$—NH—SO$_2$—NH$_2$; m is an integer from 1-20; and n is an integer from 0-8. Yet even more preferably, $R_1$ is hydrogen; $R_4$ is selected from hydrogen or alkyl; $R_2$ is hydrogen; $R_3$ is hydrogen; and X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_n$CH$_3$; m is an integer from 1-12; n is an integer from 0-4; and the C-17 hydroxyl is in the (S) configuration.

Still another embodiment of the invention, directed to a compound of a Formula Ic:

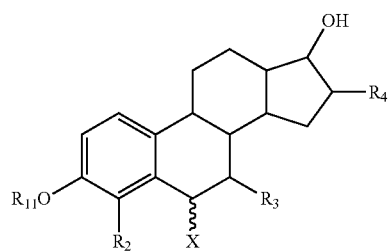

Ic wherein $R_{11}$, $R_2$, $R_3$, $R_4$ and X are as defined above for Formula I. Even more preferably, $R_{11}$ is hydrogen or $C_1$-$C_6$ alkyl; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$ N(CH$_3$)—SO$_2$—NH$_3$, and —$(CH_2)_m$—NH—SO$_2$—NH$_2$; m is an integer from 1-20; and n is an integer from 0-8. Yet even more preferably, $R_{11}$ is hydrogen; $R_4$ is selected from hydrogen or alkyl; $R_2$ is hydrogen; $R_3$ is hydrogen; and X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_n$CH$_3$; m is an integer from 1-12; n is an integer from 0-4; and the C-17 hydroxyl is in the (S) configuration.

Yet another embodiment of the present invention is directed to a compound of a Formula Id:

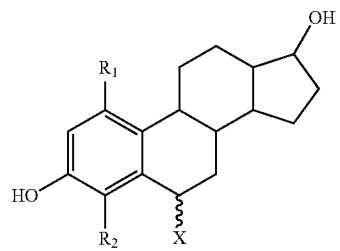

Id wherein $R_1$, $R_2$, and X are as defined above for Formula I. Even more preferably, $R_1$ is selected from hydrogen, —OH and halo; $R_2$ is selected from hydrogen and halo; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, —$(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$ N(CH$_3$)—SO$_2$—NH$_3$, and —$(CH_2)_m$—NH—SO$_2$—NH$_2$; X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_m$CH$_3$; m is an integer from 1-20; and n is an integer from 0-8. Still even more preferably, $R_1$, $R_2$, $R_3$ and $R_4$ are hydrogen; m is an integer from 1-12; n is an integer from 0-4; and the C-17 hydroxyl is in the (S) configuration.

Yet another embodiment of the present invention is directed to a compound of a Formula Ie:

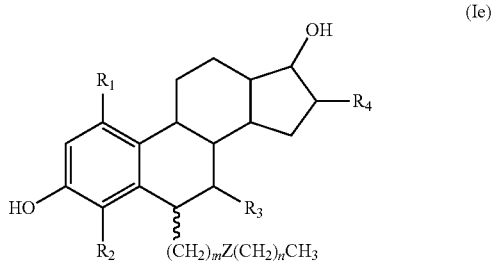

(Ie)

wherein m, n, $R_1$, $R_2$, $R_3$ and $R_4$ are as defined above for Formula I, and Z is selected from —O—, —S— and —NH—. Even more preferably, m is 1-12, n is 0-4, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and —OH; Z is selected from —O— and —S—; and the C-17 hydroxyl is in the (S) configuration.

Still another embodiment of the present invention is directed to a compound of a Formula If:

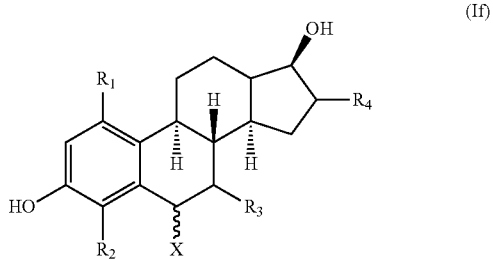

(If)

wherein $R_1$, $R_2$, $R_3$, $R_4$ and X are as defined above for Formula I. Even more preferably, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$ N(CH$_3$)—SO$_2$—NH$_3$, and —$(CH_2)_m$—NH—SO$_2$—NH$_2$; X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_n$CH$_3$; m is an integer from 1-20; and n is an integer from 0-8. Still even more preferably, $R_1$, $R_2$, $R_3$ and $R_4$ are hydrogen; m is an integer from 1-12; and n is an integer from 0-4.

Embodiment compounds of the present invention can be used in a pharmaceutical composition. Such a composition can comprise one or more compounds selected from those discussed above, illustrated below or otherwise inferred herein, and combinations thereof. In certain embodiments, such a composition can comprise a pharmaceutically-acceptable carrier component. Without limitation, such a composition can comprise a racemic mixture of compounds. In certain embodiments, such a compound can be present as the S and R enantiomer, preferably their isolated and purified form which is substantially free of other isomers, and $R_5$, or $R_7$ can be selected from H, $C_1$ to $C_6$ alkyl or substituted alkyl, and a halogen.

The compounds of the present invention may have asymmetric centers and may occur as a racemate, a racemic mixture or as individual and purified diastereomers or enantiomers such as (named via ChemDraw Ultra, Version 12.0 or similar) (8S,9S,14S,17S)-7,8,9,11,12,13,14,15,16,17-decahydro-6H-cyclopenta[a]phenanthrene-3,17-diol (compound 2); (6R,8S,9S,14S,17S)-6-(methoxymethyl)-7,8,9,11,12,13,14,15,16,17-decahydro-6H-cyclopenta[a] phenanthrene-3,17-diol (compound 1); (6R,8S,9S,14S,17S)-6-(6-methoxyhexyl)-7,8,9,11,12,13,14,15,16,17-decahydro-6H-cyclopenta[a]phenanthrene-3,17-diol (compound 3); (6R,8S,9S,14S,17S)-6-(hydroxymethyl)-7,8,9,11,12,13,14,15,16,17-decahydro-6H-cyclopenta[a]phenanthrene-3,17-diol (compound 4); (6R,8S,9S,14S,17S)-6-((aminooxy)methyl)-7,8,9,11,12,13,14,15,16,17-decahydro-6H-cyclopenta[a]phenanthrene-3,17-diol (compound 5); (6R,8S,9S,14S,17S)-6-(((methoxymethyl)amino)methyl)-7,8,9,11,12,13,14,15,16,17-decahydro-6H-cyclopenta[a]phenanthrene-3,17-diol; methyl(H6R,8S,9S,14S,17S)-3,17-dihydroxy-13-7,8,9,11,12,13,14,15,16,17-decahydro-6H-cyclopenta[a]phenanthren-6-yl)methyl)carbamate (compound 6); (6R,8S,9S,14S,17S)-6-methoxy-7,8,9,11,12,13,14,15,16,17-decahydro-6H-cyclopenta[a]phenanthrene-3,17-diol (compound 7); (6R,8S,9S,14S,17S)-6-(2-methoxyethyl)-7,8,9,11,12,13,14,15,16,17-decahydro-6H-cyclopenta[a]phenanthrene-3,17-diol (compound 8); (6R,8S,9S,14S,17S)-6-(4-methoxybutyl)-(7,8,9,11,12,13,14,15,16,17-decahydro-6H-cyclopenta[a]phenanthrene-3,17-diol (compound 9); (6R,8S,9S,14S,17S)-6-(8-methoxyoctyl)-7,8,9,11,12,13,14,15,16,17-decahydro-6H-cyclopenta[a]phenanthrene-3,17-diol (compound 10); (6R,8S,9S,14S,17S)-3-hydroxy-6-(methoxymethyl)-7,8,9,11,12,13,14,15,16,17-decahydro-6H-cyclopenta[a]phenanthren-17-yl stearate (compound 11); (6R,8S,9S,14S,17S)-6-(4-propoxybutyl)-7,8,9,11,12,13,14,15,16,17-decahydro-6H-cyclopenta[a]phenanthrene-3,17-diol (compound 12) and (6R,8S,9S,14S,17S)-6-(5-ethoxypentyl)-7,8,9,11,12,13,14,15,16,17-decahydro-6H-cyclopenta[a]phenanthrene-3,17-diol.

An embodiment of the present invention pertains to the preparation of the R or S enantiomers, and/or R or S diastereomers of 6 substituted estradiols. Methods for the preparation (e.g., asymmetric synthesis) and separation (e.g., fractional crystallization and chromatographic means) of such isomeric forms are either generally known in the art or are readily obtained by adapting the methods taught herein. Such methodologies are, for example, described in U.S. Pat. No. 7,846,918, the teachings of which are herein incorporated in its entirety.

The compounds of the present invention can be synthesized by the following methods as depicted in the schemes below. The demethylestradiol derivative 1 is prepared through the 17-one compound C, which is converted to the oxime E. The d ring of E is subsequently opened to produce the methylene propanenitrile F. The epoxide G is then formed, followed by the reformation of ring d to afford compound H. H is then reduced to produce compound 1.

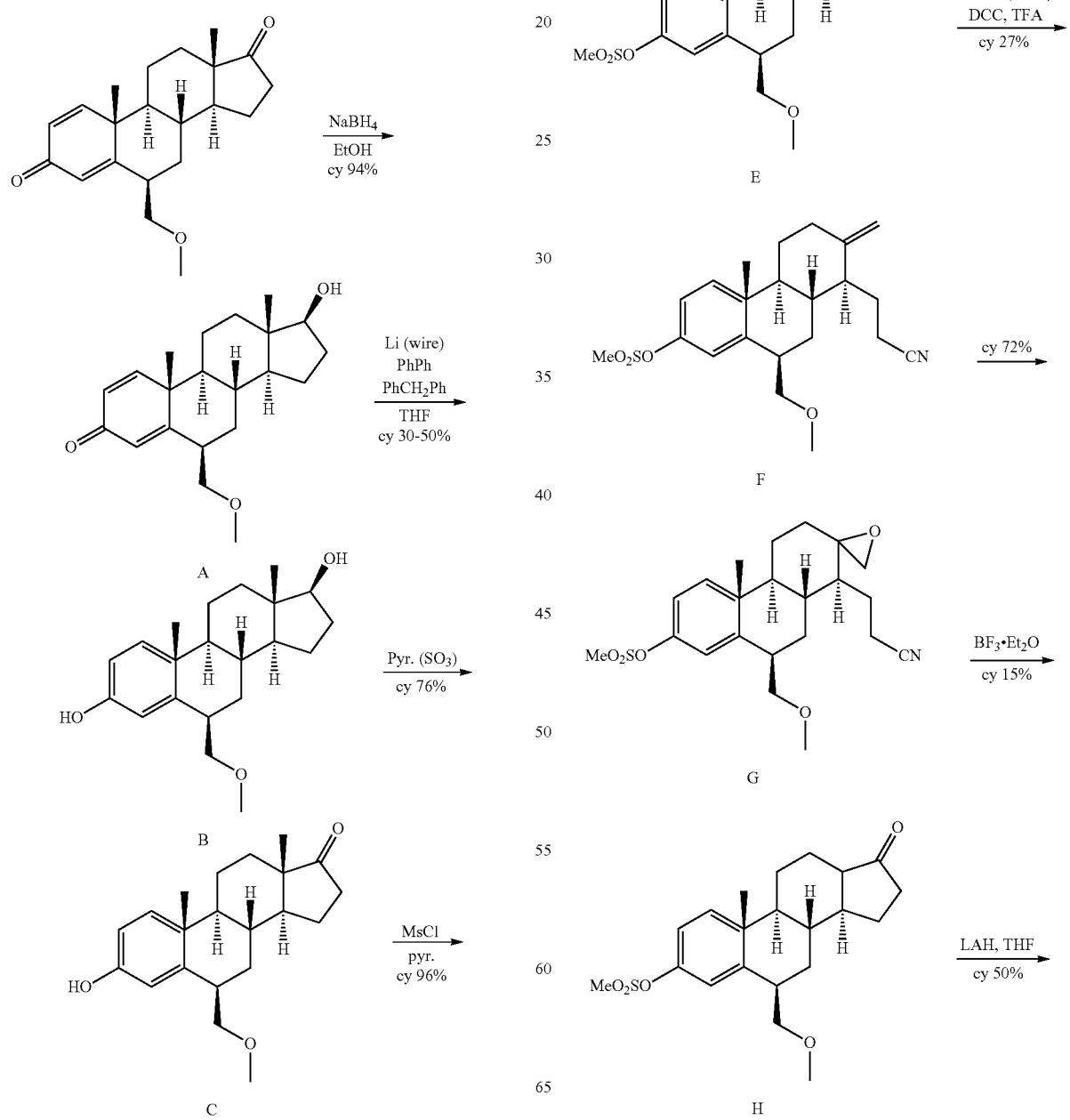

-continued

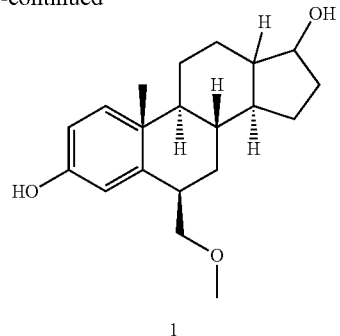

Reaction schemes for preparing estradiol derivatives is given below, Schemes 2-4. Such methods can comprise reaction of a t-butyldimethylsilyl derivative of estradiol with LIDAKOR/THF/formaldehyde to obtain a 6-hydroxylated compound followed by such steps as: (i) hydrolysis to obtain 6-hydroxymethyl derivative of estradiol; and/or (ii) treatment with dimethylsulfate followed by hydrolysis to obtain 6-methyloxymethyl derivative of estradiol.

In an alternative approach, estradiol compounds can also be prepared by a method comprising such steps as: (i) protecting an estrodial compound, (ii) acylating the protected estradiol compound at the benzylic 6-position with LIDAKOR/Butyl-Lithium/Diisopropylamine/potassium tert-amylate, (iii) reducing the position 6 aldehyde with lithium aluminum hydride, (iv) deprotecting the protected regions of the estradiol compound. A reaction scheme for preparing estradiol derivatives is given below in Scheme 2.

Scheme 2

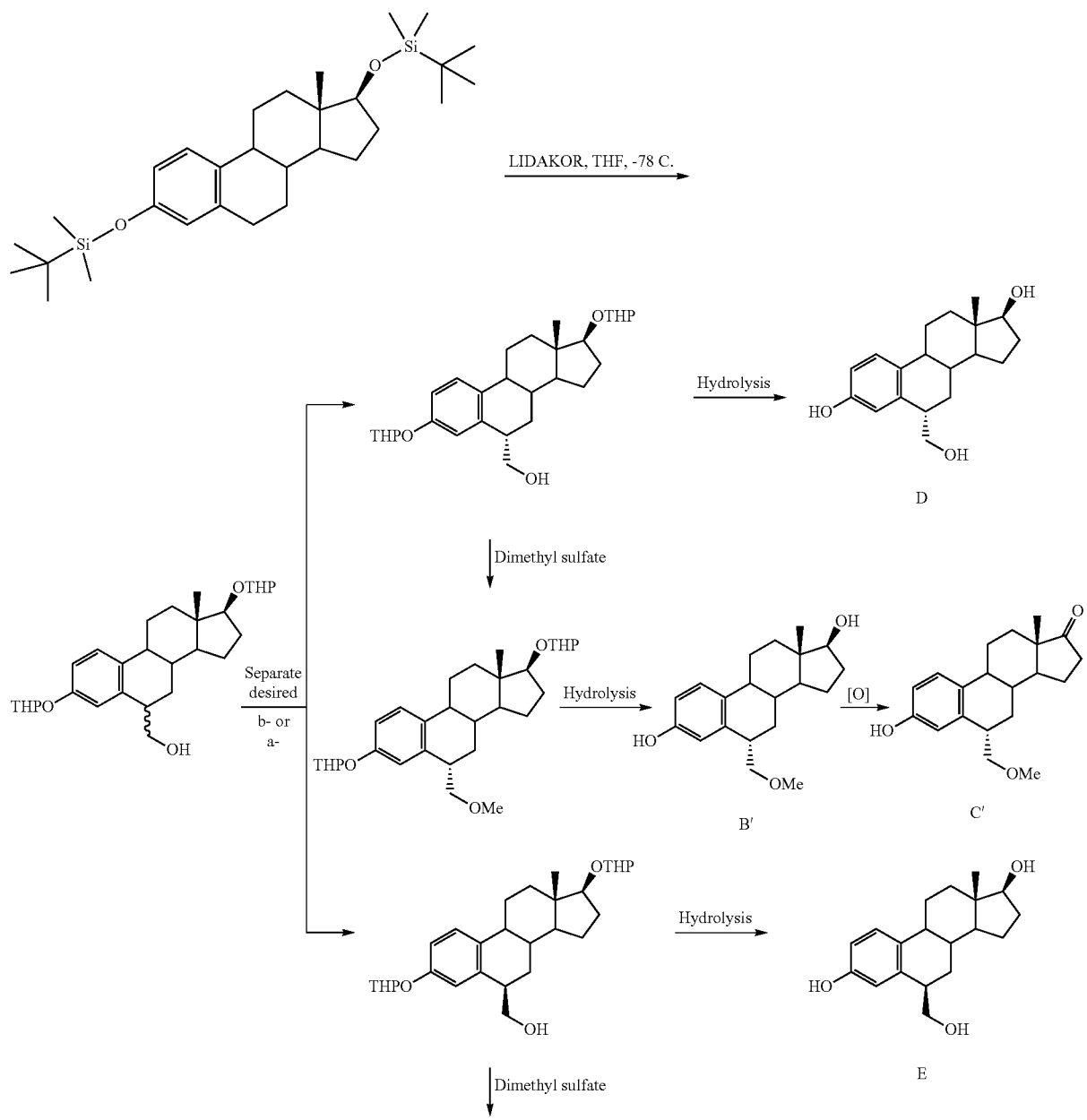

15 16
-continued
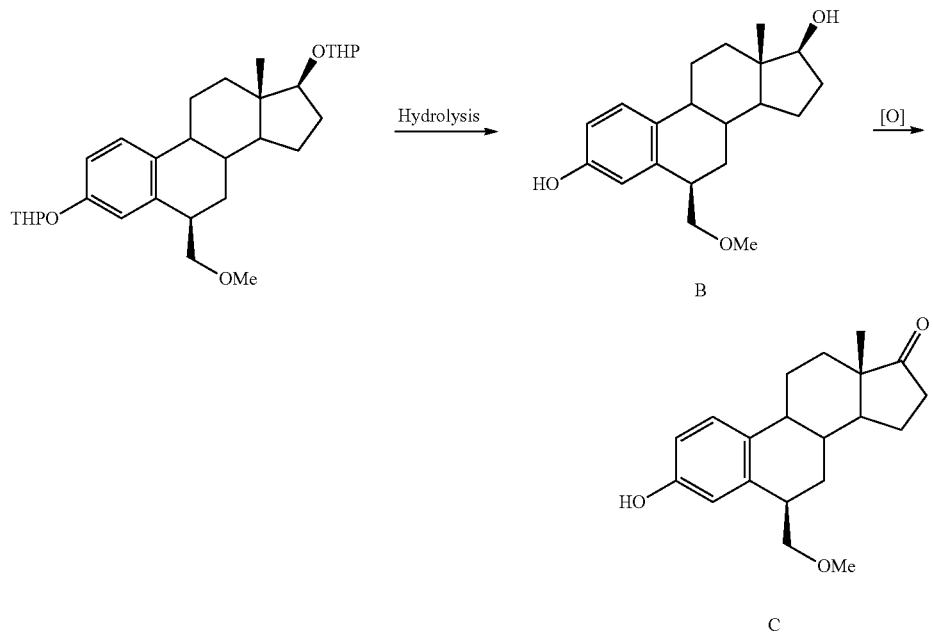
Scheme 3
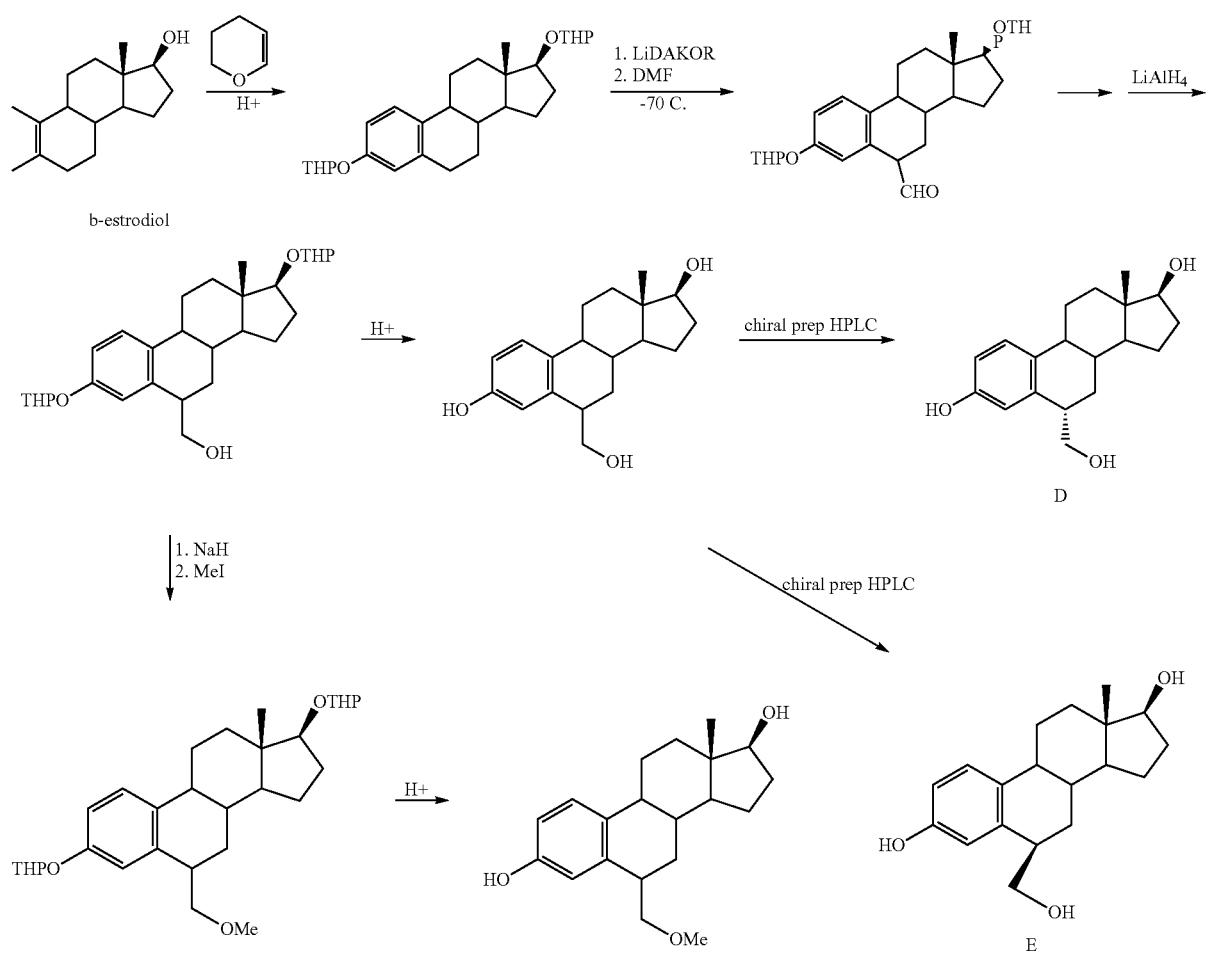

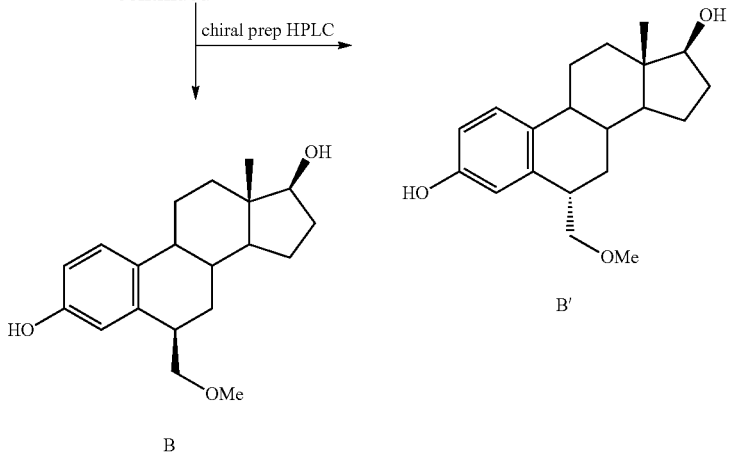

Various alkyloxyalkyl derivatives, in accordance with this invention, involve selection of alkylating agents. Such derivatives would be understood by those skilled in art made aware of this invention, and is available through synthetic procedures of the sort described herein. Accordingly, without limitation, various $C_1$ to $C_6$ alkyl and substituted alkyl reagents can be used as described herein to prepare the corresponding alkyloxyalkyl derivatives.

In another aspect of the invention, methods of making 6-amino derivatives of the estradiol are disclosed in reaction schemes below. Accordingly, 6-methoxylated estradiols described in Schemes 2-3 are employed and converted to their respective amino derivatives.

Scheme 4

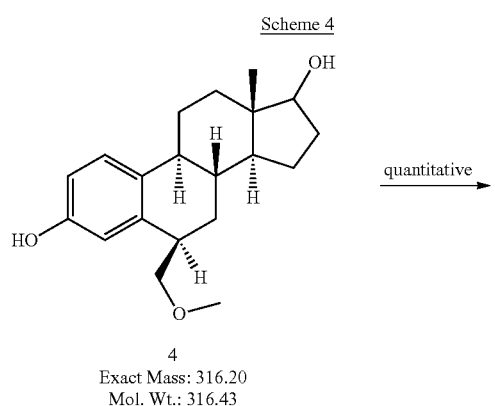

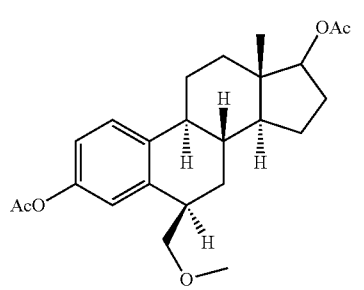

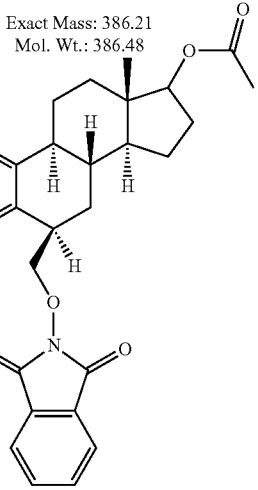

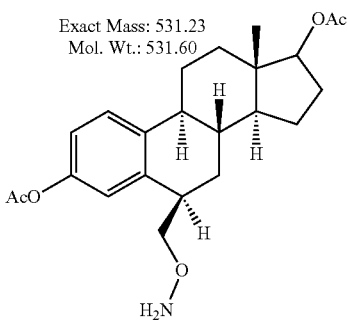

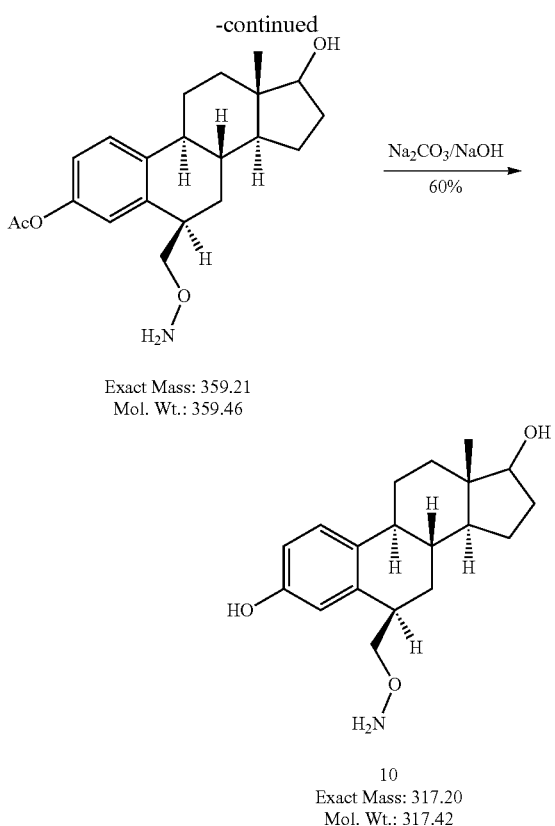

Exact Mass: 359.21
Mol. Wt.: 359.46

Exact Mass: 317.20
Mol. Wt.: 317.42

Methods of Use

The present invention relates to a method of treating pain in a mammalian subject (e.g., a human patient). In such a method, the subject is treated with a compound of Formula I, including Ia-If, or pharmaceutically acceptable salts or hydrates thereof.

In at least another aspect of the present invention, effective doses of compounds having Formula I, including Ia-If, are administered to the patients in need of such therapy.

In an aspect of the invention, the compounds disclosed herein bind specifically to only one of the aforementioned receptors. For example, the compounds of Formula I and Ia-If can be used as a specific agonist and/or antagonist of a specific estrogen receptor. In a preferred embodiment, the compounds of the invention can be used specifically as an ERβ agonist. As such, the compounds can also be used in a method for treating or preventing a disease mediated by ERβ, such as, for example, pain, immune disorders or inflammation.

In addition, administration of the compounds of the present invention for treatment of pain may comprise administration of a compound of Formula I, including Ia-If, in combination with other adjunct pain therapies. The modulation of pain through the use of ERβ agonists has been well documented, as evidenced by Spooner, M. F. et al., *Neuroscience* 150, 675-680 (2007); Piu, F. et al., *European Journal of Pharmacology* 590, 423-429 (2008); Piu, F. et al., *European Journal of Pharmacology* 592, 158-159 (2008); all of which are incorporated herein by reference.

The compounds of the invention may also be used as part of an in vitro assay, for example, in order to determine whether a candidate host is likely to benefit from treatment with the compound in question. Any active compound of the present invention may also be used as a standard, for example, in an assay, in order to identify other active compounds, other anti-proliferative agents, other anti-inflammatory agents, etc.

At least in one aspect of the instant invention, the candidate compounds are evaluated for their estrogen receptor antagonistic activity. The evaluation as to whether a compound is an estrogen receptor antagonist may be carried out by various methodologies known in the art. In the instant application, such capacity is determined by conducting the Luciferase binding assay according to the screening methods described herein.

In another embodiment of this aspect of the invention, the estrogen receptor binding capacity are assessed by transiently transfecting CV-1 cells with expression constructs for either ER(α) or ER (β) plus an ERE-tk-luciferase reporter construct. The cells are then divided into controls and candidate groups wherein the controls receive no treatment, or are treated with estradiol alone (1 nM) and the candidate groups receive estradiol plus a compound of the invention at varying concentrations. After 16-24 hours the cells are harvested and assayed for luciferase activity using a commercially available assay kit.

In yet another aspect of the instant invention, the $IC_{50}$ or the half maximal inhibitory concentration of the candidate compounds are determined to assess drug potency and potential dosing regimens for in vivo use. One of ordinary skill in the art is readily able to ascertain such information using commonly known methodologies. As it has been well described in the art, $IC_{50}$ represents and measures how much of a particular substance/molecule is needed to inhibit some biological process by 50%. In the instant case, the $IC_{50}$ of the candidate compounds are determined as the concentration that led to a response of 50% compared to the vehicle control cells.

As noted herein, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include any such salt known in the art. Where compounds of the present invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

To treat a mammalian subject, such as a human patient, an effective amount of one or more compounds of the present invention, or a pharmaceutically-acceptable salt thereof, is administered to the mammalian subject with pain. Effective dosage forms, modes of administration and dosage amounts may be determined empirically, and making such determinations is within the skill of the art. It is understood by the physician, veterinarian or clinician of ordinary skill in the art that the dosage amount will vary with the activity of the particular compound employed, intensity of the pain, the route of administration, the rate of excretion of the compound, renal and hepatic function of the patient, the duration of the treatment, the identity of any other drugs being administered to the subject, age, size and like factors well known in the medical arts. As discussed herein, the compounds of the present invention can be administered in such oral dosage forms as tablets, capsules (each of which includes sustained release or timed release formulations), pills, powders, micronized compositions, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. Again, the ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Compounds of the present invention may be administered in a single daily dose, or the total daily dosage may be administered in divided doses of two, three or four times daily.

As noted herein, the compounds of the present invention can be used in combination with other anti-nociceptive agents or other agents which will enhance the treatment regime for the mammalian subject. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly. It will be understood that the scope of combinations of the compounds of this invention with other agents useful to treat the targeted cancer condition includes in principle any combination with any pharmaceutical composition useful for treating disorders related to estrogen functioning.

It may be convenient or desirable to prepare, purify, and/or handle the active compound in the form of a prodrug. The term "prodrug" as used herein, pertains to a compound which, when metabolized, yields the desired active compound or in itself is the active compound. This includes for example adding a phosphoric acid ester moiety in suitable positions such as positions 3, 6, 10 or 17. Typically, the prodrug is inactive, or less active than the active compound, but may provide advantageous handling, administration, or metabolic properties. For example, some prodrugs are ethers of the active compound; during metabolism the ether group is cleaved to yield the active drug. Also, some prodrugs are activated enzymatically to yield the active compound, or a compound which, upon further chemical reaction, yields the active compound. Thus, in the methods of treatment of the present invention disclosed herein, the term "administering" shall encompass the treatment of the various conditions described with the compound specifically disclosed or with a compound which may not be specifically disclosed, but which converts to the specified compound in vivo after administration to the patient. Metabolites of these compounds include active species produced upon introduction of compounds of this invention into the mammalian subject.

Without being bound to any theories, it has been reported that Estradiol binds to the receptor ligand pocket of estrogen receptors (both ERα and ERβ), via the C17-OH (via His 524); and the C3-OH (via Arg 394 and Glu 353). As with Estradiol, binding of compound 1 diol, for example, in the same ligand pocket of ERα and ERβ, and preferably just ERβ, via similar amino acid bindings may occur. Additionally, the presence of the alkoxyalkyl substituent at the C-6 carbon of compound 1 may alter the conformation of the normal ligand-bound receptor resulting in modified activity accounting for the observed anti-tumor activity.

Compositions

As used herein, the term "composition" is intended to encompass a product comprising the specified ingredients in the specified amounts, as well as any product which results, directly or indirectly, from combination of the specified ingredients in the specified amounts.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethylacetate, butylalcohol, benzyl benzoate, propylene glycol, glycol, oils (in particular, cottonseed, groundnut, corn, germ, olive, castor and sesame oils), glycerol, amyl alcohol, tetrahydrofuryl polyethylene glycols and fatty acid esters of sorbitan, and mixtures thereof.

Besides inert diluents the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders sprays, ointments, pastes, creams, lotions, gels, solutions, patches and inhalants. The active ingredient(s) may be mixed under sterile conditions with pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Compounds of the present invention may be administered in intranasal form via topical use of suitable intranasal vehicles, or via transdermal routes, using those forms of transdermal skin patches well known to those of ordinary skill in the art. A transdermal delivery system provides for continuous administration throughout the dosage regimen. Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Another mode of delivery for the compounds of the present invention may be delivery via the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Pharmaceutical compositions of this invention suitable for parenteral administration comprise the active ingredient (s) in combination with one or more pharmaceutically-acceptable sterile isotonic aqueous or nonaqueous solutions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly(anhydrides). Depot injectable formulations are also prepared by entrapping the active ingredient(s) in liposomes or microemulsions which are compatible with body tissue. The injectable materials can be sterilized for example, by filtration through a bacterial-retaining filter.

Preferably the composition delivered in the form of an injectable dosage form comprise a biocompatible polymer, a compatible form of the presently disclosed compounds and a biocompatible solvent which solubilizes the biocompatible polymer wherein the weight percents of the biocompatible polymer, the instant and biocompatible solvent are based on the total weight of the complete composition; further wherein sufficient amounts of said polymer are employed in said composition such that, upon delivery to a vascular site, the polymer is able to precipitate and allow release of the active compound in doses sufficient to stop tumor growth.

Still another aspect of this embodiment would observe for appropriate viscosity of said composition, preferably in the range of about 10 to 200 cSt at 40° C.

More preferably, the composition comprises a biocompatible polymer at a concentration of from about 1 to 95 weight percent, active compound at a concentration of from about 5 to about 75 weight percent, and a biocompatible solvent from about 5 to about 95 weight percent, wherein the weight percent of the all components is based on the total weight of the complete composition and further wherein the composition has a viscosity of at least 10 to about 200 and more preferably at least about 200 cSt at 40° C.

Biodegradable polymers are disclosed in the art. For example, Dunn, et al. in U.S. Pat. No. 4,938,663, discloses the following examples of biodegradable polymers: linear-chain polymers such as polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, and copolymers, terpolymers and combinations thereof. Other biodegradable polymers include, for example, gelatin, collagen, etc.

Suitable non-biodegradable biocompatible polymers include, by way of example, cellulose acetates, ethylene vinyl alcohol copolymers, hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof.

Preferred biocompatible polymers can include acrylic polymers, cellulose diacetate and ethylene vinyl alcohol copolymer, polyethylene glycol, chitosan, collagen and gelatin. Such polymers are either commercially available or can be prepared by art recognized procedures. In a preferred embodiment, the number average molecular weight, as determined by gel permeation chromatography composition is from about 5,000 to about 200,000 more preferably from about 25,000 to about 180,000 and still more preferably from about 50,000 to 100,000.

It is still another aspect of this invention to employ a biocompatible contrast agent within the composition to observe and monitor the clinical progress of the local site of interest. These contrast agents include water soluble contrast agents and water insoluble contrast agents. Preferably, the water insoluble contrast agent is a biocompatible material selected from the group consisting of barium sulfate, tantalum powder and tantalum oxide. In still a further preferred embodiment, the biocompatible solvent is water, dimethylsulfoxide (DMSO), ethanol, ethyl lactate or acetone.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules, nanoparticles and tablets of the type described above.

The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for ampule, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam or any other methods fit to by those of ordinary skill in the art for administration to a region of interest.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The general methods given in the Schemes for the preparation of compounds exemplified in formulas I, including Ia-If, are further illustrated by the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product. All compounds are named using ChemBioDraw Ultra 11.0 or 12.0, or a similar version.

EXAMPLE 1

Methods of Preparing
6-hydroxymethyl-androsta-1,4-diene-3,17 dione

In a reaction system, sufficient amounts of (+)androsta-1,4-diene-3,17-dione (ADD), 12.2 equivalents pyrrolidine, catalytic acetic acid, denatured ethanol (95/5 ethanol/methanol) and 6-7% tetrahydrofuran (THF) are heated to 30 to 40° C. for a minimum of 16 hours to form 1,3-dipyrrolidinoandrosta-3,5-diene-17one. Once the ADD content reaches to a less than 3% by HPLC area, or it becomes static or the resulting dipyrrolidinoandrostadiene begins to revert to ADD, the reaction mixture is cooled to 5±5° C. The resulting compound is then collected and washed with cold denatured ethanol. Yields are typically 70-800 on a dry basis with purities typically 90-95% by HPLC area percent.

The resulting 1,3-dipyrrolidinoandrosta-3,5-diene-17one is then mixed in amount of 1 equivalent with 2.6 equivalents formalin (formaldehyde) in 10 ml dichloromethane/g at room temperature. The reaction mixture is then acidified to a pH of about 2 with 2% sulfuric acid solution. Accordingly, an organic layer is formed, which is washed with 2% sulfuric acid and 1:1 water/brine. Solvent exchange into toluene (approximately 10 ml/g) is then carried out wherein the product crystallizes as toluene exchange transpires. Said product is collected washed and dried to provide 6-hydroxymethyl-androsta-1,4-diene-3,17 dione. One of ordinary skill in the art can further modify the stereochemistry at position 6, if so desired, by employing known techniques in the art.

EXAMPLE 2

Methods of Preparing Compounds B and B'

As outlined in Scheme 2, estradiol compounds B and B' are synthesized in the following manner. The protected estradiol is prepared by reaction of β-estradiol with dihydropyran in THF, using toluenesulfonic acid or camphorsulfonic acid as catalyst. As one of ordinary skill in the art can appreciate, this reaction is an equilibrium reaction and would not go to completion under such conditions. Thus, both the mono-protected estradiols can be found in the reaction mixture. Such crude reaction mixture would undergo a trituration step with acetonitrile causing the desired bis-THP estradiol to crystallize in approximately 70% yield.

As shown in Scheme 2, the intermediate aldehyde is obtained via acylation at the benzylic 6-position with a strong base mixture referred to as LiDAKOR: butyl lithium, diisopropylamine, and potassium tert-amylate. Under such conditions at −70° C., one of ordinary skill in the art can appreciate the abstraction of a proton at a benzylic position. The intermediate aldehyde is then purified by column chromatography to give a syrup in approximately 50% yield. Reduction of the aldehyde with an excess of lithium aluminum hydride results in high yields of the racemic hydroxymethyl estradiol compound as a glassy foam.

For purposes of preparing compounds B and B', the methoxymethyl intermediate compound is prepared by methylation of the racemic hydroxymethyl estradiol compound with sodium hydride and methyl iodide. The methoxymethyl intermediate is purified by column chromatography to give a glassy foam. Deprotection of the protecting groups gives deprotected racemic 6-methoxymethyl estradiol. Separation of the enantiomers is performed using chiral preparative HPLC to give the compounds B and B'. For compound B, a chiral purity of >95:5 R:S is realized. For compound B', a chiral purity of 86:14 S:R is realized. It is well within the level of one of ordinary skill in the art to employ NMR for determination of the absolute stereochemistry of the 6-position, where the 4- and 6-protons are diagnostic.

EXAMPLE 3

Methods of Preparing Compounds D and E

Using the same methodologies described in Example 2, the racemic hydroxymethyl estradiol compound is synthesized. Deprotection of the same is then achieved with catalytic hydrogen chloride in methanol, and the resulting racemic triol is separated on chiral preparative HPLC to give two fractions, one enriched for compound D and the other enriched for compound E. For each compound, chiral purity of >95:5 R:S and S:R is realized respectively. Absolute stereochemistry of the 6-position is established by NMR, where the 4- and 6-protons are diagnostic.

EXAMPLE 4

(6R,8R,9S,10R,13S,14S,17S)-17-hydroxy-6-(methoxymethyl)-10,13-dimethyl-6,7,8,9,10,11,12,13,14,15,16,17-dodecahydro-3H-cyclopenta[a]phenanthren-3-one (A)—Commercially available (6R,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione (200 g, 0.608 mol) is put in a 5 L 3-necked flask and dissolved in ethanol (1.3 L) and water (400 ml). The resulting mixture is cooled to ~0° C. in an ice-water bath. Then, a solution of NaBH$_4$ (12% wt in 40% NaOH, 42.5 ml, 0.182 mol) is added drop-wise, keeping the temperature beneath 5° C. The resulting mixture is stirred for 2 hours at <10° C. The reaction mixture is checked by LC-MS which shows ~95% conversion+~50 over-reduction. Next, the reaction mixture is quenched with water (400 ml) and the pH is adjusted to pH 3-4 by addition of 6N aq. HCl solution. The mixture is subsequently transferred to a 3 L round bottom flask and the volatiles are removed under reduced pressure. The residual aqueous mixture is extracted with TBME (3×500 ml). The combined organic layers are washed with sat. aq. NaHCO₃ (1 L), water (1 L) and brine (1 L). Finally, the organic layer is dried over Na₂SO₄, filtered and concentrated under reduced pressure to furnish the dienone A as a pale yellow solid. (188 g, cy 94%). Product identified via ¹HNMR and HPLC-MS. ~95%+~5% over-reduction.

EXAMPLE 5

Methods of Preparing (6R,8R,9S,13S,14S)-6-(6-methoxyhexyl)-13-methyl-7,8,9,11,12,13,14,15,16,17-decahydro-6H-cyclopenta[a]phenanthrene-3,17-diol (I)

a) (8R,9S,13S,14S,17S)-3,17-bis(methoxymethoxy)-13-methyl-7,8,9,11,12,13,14,15,16,17-decahydro-6H-cyclopenta[a]phenanthrene—Chloromethyl methyl ether (7.0 mL, 92.0 mmol) is added to a solution of β-estradiol (5 g, 18.4 mmol) and diisopropylethylamine (16.0 mL 92 mmol) in 100 mL of THF. The reaction mixture is heated to reflux and stirred for 18 hours. The THF is removed in vacuo, and the yellow/brown oil is partitioned between water and CH₂Cl₂. The organic layer is separated, washed with brine, dried (Na₂SO₄), filtered, and evaporated in vacuo to give a golden oil. Purification by silica gel column chromatography (10% EtOAc/Hex) affords the title compound as a viscous, clear oil (5.7 g, 86%).

b) (8R,9S,13S,14S,17S)-3,17-bis(methoxymethoxy)-13-methyl-7,8,9,11,12,13,14,15,16,17-decahydro-6H-cyclopenta[a]phenanthren-6-ol—To a solution of potassium tert-butoxide (8.87 g, 79.0 mmol) and diisopropylamine (11.2 mL, 79.0 mmol) in 80 mL of anhydrous THF cooled to −78° C. under argon is added n-butyllithium (49.4 mL, 79.0 mmol, 1.6 M in hexane) dropwise. The reaction mixture is stirred at −78° C. for 30-45 minutes. A solution of the compound from a) (5.7 g, 15.8 mmol) in 45 mL of THF is then added dropwise, and the reaction mixture is stirred for 3 hours at −78° C. During the addition of the compound from a), the reaction turns a deep red color. Trimethyl borate (10.6 mL, 94.8 mmol) is then added slowly, and the mixture is warmed to 0° C. and stirred for 2 hours. Hydrogen peroxide (24 mL of a 30% aq. solution) is then added, and the reaction mixture is warmed to room temperature and stirred for a further 1 hour. The reaction is cooled back to 0° C. and carefully quenched with a 10% aq. Na₂S₂O₃ solution (70 ml). The resulting mixture is extracted with EtOAc (2×), and the combined organic extracts are dried (Na₂SO₄), filtered, and evaporated in vacuo to give a yellow/brown oil. Purification by silica gel column chromatography (256 EtOAc/Hex) affords the title compound as a white solid (3.5 g, 59%).

c) (8R,9S,13S,14S,17S)-3,17-bis(methoxymethoxy)-13-methyl-7,8,9,11,12,13,14,15,16,17-decahydro-6H-cyclopenta[a]phenanthren-6-one—Dess-Martin Periodinane (9.46 g, 22.3 mmol) is added portionwise to a solution of the compound from b) (7.0 g, 18.6 mmol) in 300 mL of CH₂Cl₂. The resulting reaction mixture stirred at room temperature for 3 hours. The mixture is poured into water and the layers are separated. The aqueous layer is extracted with CH₂Cl₂, and the combined organic extracts are washed with brine, dried (Na₂SO₄), filtered, and evaporated in vacuo to give a gooey, brown solid. Purification by silica gel column chromatography (15%) EtOAc/Hex) affords the title compound as a pale yellow, viscous oil (6.0 g, 86%).

d) ethyl 2-(((8R,9S,13S,14S,17S)-3,17-bis(methoxymethoxy)-13-methyl-7,8,9,11,12,13,14,15,16,17-decahydro-6H-cyclopenta[a]phenanthren-6-ylidene)acetate-Triethyl phosphonoacetate (4.1 mL, 20.8 mmol) is added to a mixture of sodium hydride (832 mg, 20.8 mmol) in 25 mL of THF at room temperature. After approximately 10 minutes, a solution of the compound from c) (3.9 g, 10.4 mmol) in 10 mL of THF is added dropwise. The resulting reaction mixture is heated to reflux in a sealed tube for hours. The mixture is concentrated in vacuo and purified by silica gel column chromatography (gradient from 5% EtOAc/Hex to 40% EtOAc/Hex) to give the title compound as a clear, viscous oil (3.4 g, 74%).

e) 2-((8R,9S,13S,14S,17S)-3,17-bis(methoxymethoxy)-13-methyl-7,8,9,11,12,13,14,15,16,17-decahydro-6H-cyclopenta[a]phenanthren-6-ylidene)ethanol—A solution of the compound from d) (3.1 g, 6.97 mmol) in 65 mL of THF is treated with lithium aluminum hydride (5.2 mL, 10.46 mmol, 2 M in THF) dropwise at 0° C. The cold bath is removed, and the reaction mixture is stirred at room temperature for 15 minutes. The reaction is cooled back to 0° C. and quenched by the careful addition of 1.3 mL of water, followed by 2.6 mL of 2N NaOH, and then 1.3 mL of water. The mixture is stirred vigorously until a white solid forms. The mixture is filtered, and the filtrate is concentrated in vacuo to give the title compound as a clear oil (2.8 g, 99%).

f) 2-((6S,8R,9S,13S,14S,17S)-3,17-bis(methoxymethoxy)-13-methyl-7,8,9,11,12,13,14,15,16,17-decahydro-6H-cyclopenta[a]phenanthren-6-yl)acetaldehyde—A mixture of the compound from e) (3.09 g, 7.68 mmol) and 10% Pd/C (500 mg) in 100 mL of ethyl acetate is stirred under 40 psi of H₂ (g) for 5 hours at room temperature. The mixture is filtered through Celite, and the Celite is washed well with ethyl acetate. The filtrate is concentrated in vacuo to give a pale yellow oil (3.1 g). The oil is dissolved in 100 mL of dichloromethane, and Dess-Martin Periodinane (3.9 g, 9.22 mmol) is added portionwise. The resulting reaction mixture is stirred at room temperature for 30 minutes. The mixture is poured into water and extracted with CH₂Cl₂. The combined organic extracts are washed with brine, dried (Na₂SO₄), filtered, and evaporated in vacuo to give a brown solid. Purification by silica gel column chromatography (15% EtOAc/Hex) affords the title compound as a clear oil (2.0 g, 65%).

g) 4-((6R,8R,9S,13S,14S,17S)-3,17-bis(methoxymethoxy)-13-methyl-7,8,9,11,12,13,14,15,16,17-decahydro-6H-cyclopenta[a]phenanthren-6-yl)but-2-en-1-ol—Lithium bis(trimethylsilyl)amide (18.4 mL, 18.4 mmol, 1.0 M in THF) is added dropwise to a suspension of (2-hydroxyethyl)triphenylphosphonium bromide (3.37 g, 8.70 mmol) in 60 mL of THF at 0° C. After 1 hour, the golden brown solution is treated with a solution of the compound from f) (1.4 g, 3.48 mmol) in 10 mL of THF dropwise. The resulting reaction mixture is stirred at 0° C. for 40 minutes and then quenched with saturated aqueous NH₄Cl. The resulting mixture is extracted with EtOAc (2×), and the combined organic extracts are dried (Na₂SO₄), filtered, and evaporated to give a brown oil. Purification by silica gel column chromatography (gradient from 20% EtOAc/Hex to 75% EtOAc/Hex) affords the title compound as a yellow, viscous oil (680 mg, 45%).

h) 4-((6R,8R,9S,13S,14S,17S)-3,17-bis(methoxymethoxy)-13-methyl-7,8,9,11,12,13,14,15,16,17-decahydro-6H-cyclopenta[a]phenanthren-6-yl)but-2-enal—Dess-Martin Periodinane (437 mg, 1.03 mmol) is added to a solution of the compound from g) (370 mg, 0.86 mmol) in mL of CH₂Cl₂ at room temperature. The resulting reaction mixture is stirred for 10 minutes and then poured into water. The layers are separated and the aqueous layer is extracted with CH₂Cl₂ (2×). The combined organic extracts are washed with brine, dried (Na₂SO₄), filtered, and evaporated in vacuo to give a brown oil. Purification by silica gel column chromatography (gradient from 5% EtOAc/CH2Cl2 to 10% EtOAc/CH$_2$Cl$_2$) affords the title compound as a pale yellow, viscous oil (358 mg, 86%).

i) 6-((6R,8R,9S,13S,14S,17S)-3,17-bis(methoxymethoxy)-13-methyl-7,8,9,11,12,13,14,15,16,17-decahydro-6H-cyclopenta[a]phenanthren-6-yl)hexa-2,4-dien-1-ol—Lithium bis(trimethylsilyl)amide (4.3 mL, 4.29 mmol, 1.0 M in THF) is added dropwise to a suspension of (2-hydroxyethyl)triphenylphosphonium bromide (786 mg, 2.03 mmol) in 14 mL of THF at 0° C. After 30 minutes, the golden brown solution is treated with a solution of the compound from h) (345 mg, 0.81 mmol) in 2 mL of THF dropwise. The resulting reaction mixture is stirred at 0° C. for 20 minutes and quenched with saturated aqueous NH$_4$Cl. The resulting mixture is extracted with EtOAc (2×), and the combined organic extracts are dried (Na$_2$SO$_4$), filtered, and evaporated to give a brown oil. Purification by silica gel column chromatography (gradient from 5% EtOAc/CH$_2$Cl$_2$ to 40% EtOAc/CH$_2$Cl$_2$) affords the title compound as a yellow, viscous oil (140 mg, 38%).

j) (6R,8R,9S,13S,14S,17S)-6-(6-methoxyhexa-2,4-dien-1-yl)-3,17-bis(methoxymethoxy)-13-methyl-7,8,9,11,12,13,14,15,16,17-decahydro-6H-cyclopenta[a]phenanthrene—A solution of the compound in i) (135 mg, 0.3 mmol) is cooled to 0° C., and sodium hydride (120 mg, 3.0 mmol) is added portionwise. After 5-minutes, iodomethane (0.19 mL, 3.0 mmol) is added dropwise, and the resulting reaction mixture is warmed to room temperature and stirred for 4 hours. EtOAc is added and the reaction is carefully quenched with water. The layers are separated and the organic layer is dried (Na$_2$SO$_4$), filtered, and evaporated to give a brown oily residue. Purification by silica gel column chromatography (gradient from 5% EtOAc/Hex to 20% EtOAc/Hex) affords the title compound as a clear oil (92 mg, 65%).

k) (6R,8R,9S,13S,14S,17S)-6-(6-methoxyhexyl)-3,17-bis(methoxymethoxy)-13-methyl-7,8,9,11,12,13,14,15,16,17-decahydro-6H-cyclopenta[a]phenanthrene—A mixture of the compound in j) (90 mg, 0.19 mmol) and 10% Pd/C (100 mg) in 5-10 mL of ethyl acetate is stirred under a balloon of H$_2$ (g) for 16 hours at room temperature. The mixture is filtered through Celite, and the Celite is washed well with ethyl acetate. The filtrate is concentrated in vacuo to give the title compound as a clear oil (90 mg, 99%).

l) (6R,8R,9S,13S,14S)-6-(6-methoxyhexyl)-13-methyl-7,8,9,11,12,13,14,15,16,17-decahydro-6H-cyclopenta[a]phenanthrene-3,17-diol (I)—A solution of the compound from k) (90 mg, 0.19 mmol) in 1.5 mL each of 6 N HCl and THF is stirred for 5 hours at room temperature. The reaction mixture is diluted with water and extracted with EtOAc (2×). The combined organic extracts are dried (Na$_2$SO$_4$), filtered, and evaporated in vacuo to give a clear, oily residue. Purification by silica gel column chromatography (gradient from CH2Cl2 to 30% EtOAc/CH2Cl2) afforded I as a white solid foam (38 mg, 52%).

EXAMPLE 6

(6R,8R,9S,13S,14S,17S)-6-(methoxymethyl)-13-methyl-7,8,9,11,12,13,14,15,16,17-decahydro-6H-cyclopenta[a]phenanthrene-3,17-diol (B)—A 20 L flange flask is placed in a heating coil and equipped with condenser cooler with N$_2$-gas inlet on top, mechanical stirrer, stirring rod+blade, and two glass-stoppers. Then, the setup is heated for 3 hours at 190° C. and placed under N$_2$-atmosphere over the weekend. The N$_2$-gas inlet is replaced by an Argon inlet and the setup is placed under an Argon bleed. The flask is charged with anhydrous THF (4 L, new bottle). Lithium wire (28.8 g, 4.61 mol, stored in mineral oil) is then cut into small pieces (~0.3 cm) and the oil is removed by stirring the pieces with heptane under N2-gas atmosphere. The heptane is decanted and the Lithium pieces are added to the stirred THF in the reaction flask. Biphenyl (175.8 g, 1.14 mol) is added in one lot whereupon a reaction takes place at the surface of the Lithium pieces furnishing a green color which disappears immediately upon stirring. After 5 minutes stirring, the green color reappears. Diphenylmethane (95.9 g, 0.57 mol) is then added in one lot. The resulting deep green mixture is heated to reflux (external temperature first at 130° C. until reaction mixture starts to reflux, then continue to reflux at an external temperature of 108° C.) followed by the drop-wise addition of a solution of the dienone A (188.7 g, 0.57 mol) in 1 L anhydrous THF. After 60 minutes the addition is completed and a yellow/brown sticky solid is obtained. The heat is turned off allowing the reaction mixture to cool to <40° C. within 2 hours. The reaction mixture is quenched by adding MeOH (300 mL) over a period of 15 minutes wherein a thick, jelly-like yellow mixture is formed. Next, the reaction mixture is brought to pH 2-4 by drop-wise addition of a 6M HCl solution over a period of 1 hour. A yellow mixture is furnished. This mixture is diluted with water (2 L) and stirred for 15 minutes. The resulting two-phase mixture is transferred to a 20 L round bottom flask and volatiles (THF/MeOH) are removed under reduced pressure. The remaining acidic aqueous phase is extracted with t-butyl methyl ether (TBME) (2 L) and the lower aqueous phase is separated (TBME layer contains mostly biphenyl and diphenyl). The Organic phase is washed with water (1 L). Then, the organic layer is washed with 2M KOH solution (2×1 L) and with water (1 L). The pH of the combined basic aqueous layers is brought to pH 2-4 (pH-paper) by addition of 6M HCl. When the appropriate pH is reached, a solid precipitates and the mixture becomes off-white. TBME (1500 mL) is added, and after stirring for 15 minutes a clear yellow organic layer and a cloudy yellowish aqueous layer form. The mixture is transferred to a separatory funnel and another 1 L TBME is added to the separatory funnel before the mixture is shaken vigorously. The two clear layers are separated. The aqueous layer is extracted a $2^{nd}$ time with TBME (1 L) and both organic extract layers are combined. The combined organic layers are washed with saturated aqueous NaHCO$_3$ solution (1 L), water (1 L) and brine (1 L). The organic layer is dried over Na$_2$SO$_4$, filtered and concentrated in vacuo to furnish a pale yellow solid B (117 g crude product).

EXAMPLE 7

(6R,8R,9S,13S,14S)-3-hydroxy-6-(methoxymethyl)-13-methyl-7,8,9,11,12,13,15,16-octahydro-6H-cyclopenta[a]phenanthren-17(14H)-one (C)—To a solution of B (20 g, 60 mmol) in DMSO (200 mL) and dichloromethane (DCM) (200 mL) at 5° C. is added triethylamine (56 mL 0.4 mol). Next, sulfur trioxide pyridine complex (40 g, 0.25 mol) is slowly added over 15 minutes. The temperature is kept between 0° C. and 5° C. during this time. The mixture is then added to 200 mL water-ice and acidified to pH<1 with 6N HCl solution. The resulting mixture is extracted four times with DCM (4×100 mL). The combined organics are dried over anhydrous sodium sulfate, filtered, and concentrated. This reaction is repeated 4× (total 56 g B as starting material). The crude material is purified by silica gel column chromatography (2/3 EtOAc/Hex) to provide the title compound as a white solid 43 g (C) (76%).

EXAMPLE 8

(6R,8R,9S,13S,14S)-6-(methoxymethyl)-13-methyl-17-oxo-7,8,9,11,12,13,14,15,16,17-decahydro-6H-cyclopenta[a]phenanthren-3-yl methanesulfonate (D)—Methanesulfonyl chloride (27 mL, 0.35 mol) is added dropwise to a solution of compound C (43.6 g, 0.139 mol) in pyridine (270 mL) at 0° C. The reaction is stirred at room temperature for 90 minutes, followed by the addition of water. A precipitate is subsequently formed. After filtration, the solid is dissolved in DCM, dried over anhydrous sodium sulfate, filtered, and concentrated to provide compound D (57.1 g, quantitative) as white solid.

EXAMPLE 9

(6R,8R,9S,13S,14S)-17-(hydroxyimino)-6-(methoxymethyl)-13-methyl-7,8,9,11,12,13,14,15,16,17-decahydro-6H-cyclopenta[a]phenanthren-3-yl methanesulfonate (E)—Hydroxylamine hydrochloride (30.31 g, 470 mmol) and sodium acetate (60 g, 820 mmol) are added to a solution of compound D (57.1 g, 146 mmol) in anhydrous ethanol (800 mL). The reaction is refluxed for 90 minutes and cooled to room temperature over night. The reaction mixture is then diluted with water and ethyl acetate. The resulting layers are separated and the aqueous layer is extracted with ethyl acetate. The combined organic layers are washed with saturated aqueous sodium bicarbonate and brine. The solution is dried over anhydrous sodium sulfate, filtered, and concentrated to provide the title compound E (47 g, 80%) as a white solid.

EXAMPLE 10

(4bS,8S,8aS,10R)-8-(2-cyanoethyl)-10-(methoxymethyl)-7-methylene-4b,5,6,7,8,8a,9,10-octahydrophenanthren-2-yl methanesulfonate (F)—Trifluoroacetic acid (1.3 mL) is added dropwise to a solution of Compound E (10 g, 24.5 mmol) and N,N-dicyclohexylcarbodiimide (15 g, 73.7 mmol) in anhydrous DMSO (50 mL) and carbontetrachloride (50 mL) at 0° C.-5° C. After 2.5 hours, ice cold water is added and the mixture is extracted three times with DCM. The combined organic layers are washed with water, saturated aqueous sodium bicarbonate, and brine. The solution is dried over anhydrous sodium sulfate, filtered, and concentrated. The reaction is performed on 2×8 g scale and 2×5 g scale. The combined crude material is purified by silica gel column chromatography (50% EtOAc/Hex) to provide the title compound F (11.9 g, 27%) as a clear oil. The by-product is isolated and HNMR is available.

EXAMPLE 11

(1'S,4a'S,9'R,10a'R)-1'-(2-cyanoethyl)-9'-(methoxymethyl)-3',4',4a',9',10',10a'-hexahydro-1'H-spiro[oxirane-2,2'-phenanthren]-7'-yl methanesulfonate (G)—m-Chloroperoxybenzoic acid (8 g, 32.3 mmol) is added in portions to a solution of compound F (4.2 g, 11.78 mmol) in DCM (150 mL) and the reaction is stirred at room temperature for 2 hours. The reaction mixture is washed with 10% aqueous potassium iodide, 1 M aqueous sodium hydrosulfite, saturated aqueous sodium bicarbonate, and brine. The solution is then dried over anhydrous sodium sulfate, filtered, and concentrated. The reaction is repeated 2× (3.9 g and 3.8 g). The combined crude material is purified by silica gel column chromatography (1:4 to 1:1 EtOAc/Hex) to provide the title compound G (8.8 g, 72% yield).

EXAMPLE 12

(6R,8S,9S,14S)-6-(methoxymethyl)-17-oxo-7,8,9,11,12,13,14,15,16,17-decahydro-6H-cyclopenta[a]phenanthren-3-yl methanesulfonate (H)—Boron trifluoride etherate (2.28 mL, 16.9 mmol) is added to a solution of compound G (1.36 g, 3.3 mmol) in anhydrous toluene (22 mL). The reaction is heated to 100° C. in microwave for 15 minutes. After cooling to room temperature, a hard solid is formed. After separation of toluene from solid, the solid is treated with saturated aqueous sodium bicarbonate and ethyl acetate (EA). The organic layer is dried over anhydrous sodium sulfate, filtered, and concentrated. This reaction is repeated (1.4 g, 0.613 g, 0.87 g, 1.1×4 g). The crude material is purified by silica gel column chromatography (5-50% EtOAC:/Hex) to provide the title compound H (1.41 g, 15%).

EXAMPLE 13

(6R,8S,9S,14S)-6-(methoxymethyl)-7,8,9,11,12,13,14,15,16,17-decahydro-6H-cyclopenta[a]phenanthrene-3,17-diol (1)—Lithium Aluminum Hydride (700 mg, 18.45 mmol) is added to a solution of compound H (550 mg, 1.45 mmol) in THF (10.0 mL) at 0° C. The reaction is refluxed for 1 hour. The reaction is then quenched with Na/K tartrate and extracted three times with ethyl acetate (3×100 mL) and DCM (3×100 mL). The organic layer is washed with 5N HCl (10 mL) and the aqueous layer is extracted with EA (2×50 mL). The combined organic layers are dried over anhydrous sodium sulfate, filtered, and concentrated. The crude material is purified by silica gel column chromatography (0-50% EtOAc/Hex) to provide the title compound in 50% yield of 1 (220 mg). The same reaction is repeated with 510 mg of compound H and another 150 mg of product is isolated.

EXAMPLE 14

Methods of Determining Estrogen Receptor Binding Capacity Using Luciferase Activity Estrogen receptor-negative CV-1 kidney cells are maintained in Dulbecco's modified Eagle's medium with 4.5 g/L glucose supplemented with 10% fetal bovine serum and 100 units/ml penicillin-streptomycin at 37° C. in a humidified 5% $CO_2$ atmosphere. The cells are then plated in 6-well dishes at a density of $2\times10^5$ cells per well in phenol-red free Dulbecco's modified Eagle's medium containing 10% charcoal-dextran-stripped fetal bovine serum. CV-1 cells are transfected using LipofectAMINE reagent according to the manufacturer's protocol. Transfections containing 1.5 ug of reporter plasmid (containing ERE-tk-luciferase containing a single ERE cloned upstream of the thymidine kinase promoter and luciferase gene) and 0.5 ug of either ERα or ERβ expression vector (containing CMV-ERα or CMV-ERβ full length coding sequence respectively). The next day, cells receive no treatment (controls) or are treated with estradiol alone (1 nM) or estradiol plus a compound of the invention (at varying concentrations). After 16-24 hours, cells are harvested and assayed for luciferase activity.

At the outset, cell monolayers are washed twice with ice-cold phosphate-buffered saline and incubated for 15 minutes in 250 μl of 1× cell culture lysis reagent (Promega, Madison, Wis.). Cell extracts are transferred to a fresh tube and assayed using the luciferase assay system (Promega). For each assay, 10 μl of extract is diluted with 90 μl of 1× cell culture lysis reagent. Luminescence is read using an AutoLumat LB953 luminometer.

A compound or a salt thereof, which is identified by the binding assay described herein, is a compound that inhibits the binding of estrodial at the ligand binding site of the estrogen receptors. Specifically, it is a compound or a salt thereof that is envisioned to cause cell proliferation statasis and accordingly exerts its pharmacological activity.

CV-1 cells are transfected with two plasmid constructs, the reporter construct ERE-tk-luciferase and a CMV-ER-β construct. Transfected control (Ctrl) CV-1 cells receive no treatment while estradiol treated cells receive estradiol E2) added alone at $10^{-9}$ M (1 nM). In the case of the compounds of the invention, each compound respectively is either added alone at $10^{-9}$ M (10 nM) or at $10^{-8}$ M plus $10^{-9}$ M estradiol (E2).

EXAMPLE 15

Method of Determining the $IC_{50}$ Values of the Candidate Compounds

The cell lines listed are maintained at approximately 5% $CO_2$, 37° C., 95% relative humidity in the media appropriate for that cell line. The cells are sub-cultured every two to three days and plated in clear bottom 96-well plates at a density of $1 \times 10^4$ cells/well and incubated at ca. 5% $CO_2$, 37° C. overnight prior to initiation of the assay. To begin cell viability assays, the media in the cell plate (100 μL) is replaced with fresh media (100 μL). The test articles are serially diluted 1:2 in fresh media in duplicate and added to the cells (100 μL) at final sample concentrations of 0.46, 1.37, 4.12, 12.35, 37.04, 111.1, 333.3 and 1000 μM (≤1% DMSO) in a total volume of 200 μL. Wells containing no cells and wells containing cells lysed with 0.1% Triton-X are used for baseline controls. Tamoxifen is used as a known control for each assay and DMSO only will be run as vehicle control. The samples are incubated at ca. 37° C. in humidified 5% $CO_2$ atmosphere for 72 hours. The plate is monitored once a day during the incubation period, paying special attention to the level of confluence. If the cells approach confluence prior to the end of the 72 hour incubation period, the experiment is terminated and cell viability measured as described below.

Cell viability is determined using a commercially available kit to determine ATP levels by luminescence. Briefly, the cell plate has the media removed and replaced with 100 μL of fresh media, and the buffer and lyophilized substrate are equilibrated to room temperature. The buffer is used to reconstitute the substrate just prior to addition to the wells of the cell plate (100 μL per well). The plate is placed into the Infinite M200 plate reader, allowed to shake for 10 minutes followed by a 10 minute wait period. The plate is then read using an integration time of 0.5 sec with no attenuation.

The mean baseline controls (wells with Triton X-100 or no cells) are subtracted from the total luminescence to give the net luminescence for that well. This total is compared to the control of DMSO only. An $IC_{50}$ is calculated as the concentration that led to a response of 50% compared to the vehicle control cells. Accordingly, those of ordinary skill in the art can appreciate that the R configuration (at C-6) of the instantly claimed composition are superior to other stereoisomers.

Table I gives the binding affinity of B, I, 1 and E2 to estrogen receptors using recombinant ERα and ERβ. Recombinant ER's are incubated with $^3$H-E2 in the presence or absence of test compounds over night at 4° 0.

Figure 2:
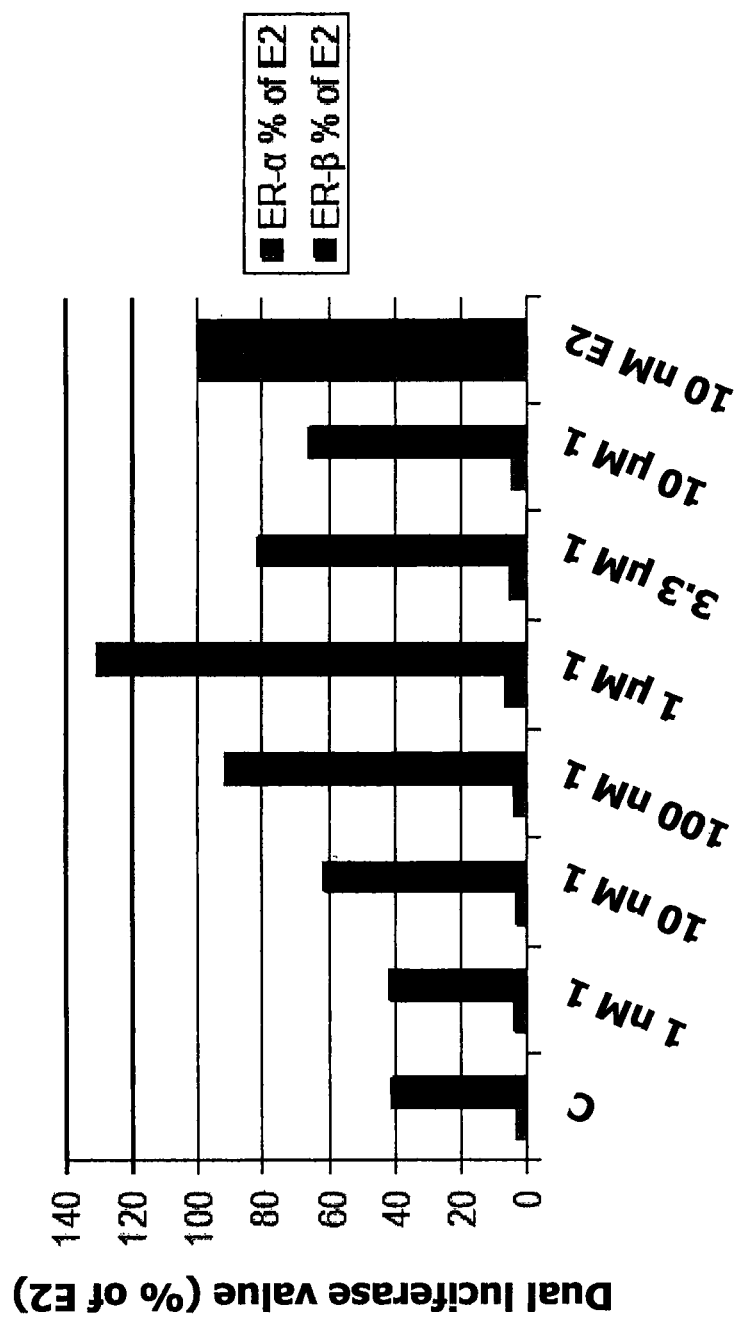
FIG. 2 depicts the % of E2 activity for I and B on ERα and ERβ.

FIG. 1 is a graph of the $EC_{50}$ values of B (I, 1 and Tamoxifen in various cell lines for compounds of the invention. FIG. 2 depicts the % of E2 activity for I and B on ERα and ERβ.

Figure 3:
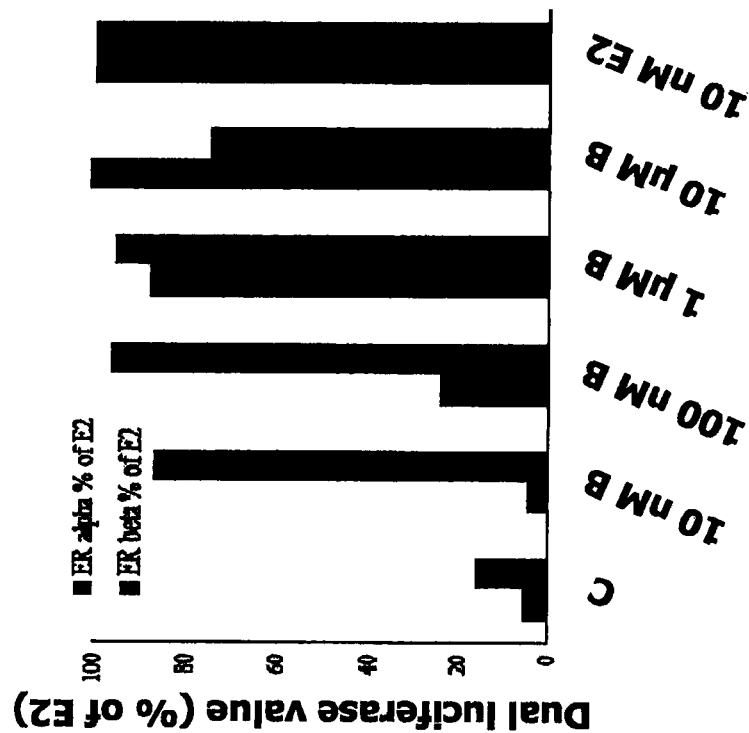
FIG. 3 depicts the response of (A) compound I and (B) compound B on ERα and ERβ measured by a luciferase assay.
Figure 3:
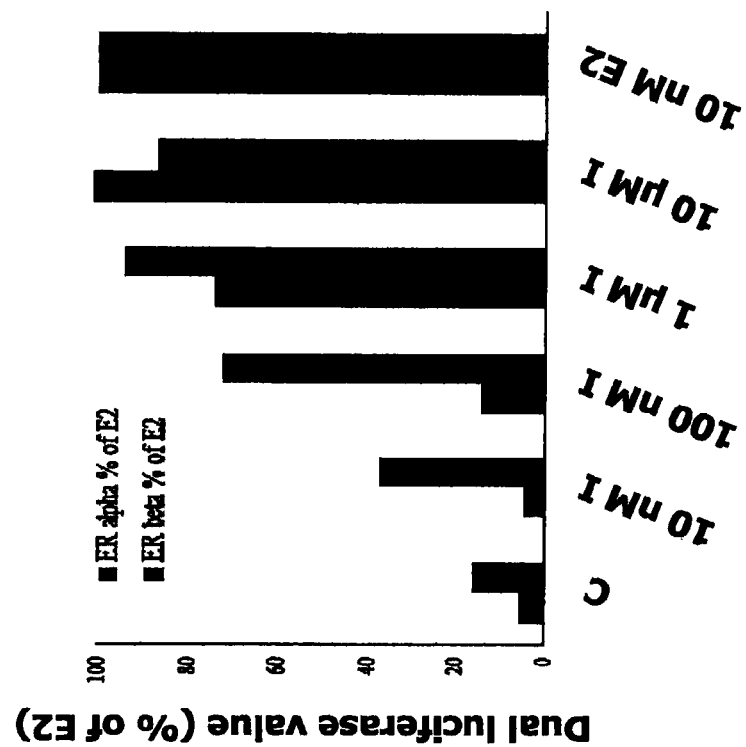

Response of I and B on ERα and ERβ is measured by a luciferase assay. MDA-MB-231 cells are transiently transfected with expression vectors encoding either ERα or ERβ and co-transfected with a luciferase reporter construct. Cells are treated for 24 hours at 37° 0 with increasing amounts of test article. In comparison, FIG. 3 shows the % of E2 activity for 1 on ERα and ERβ. As can be seen from FIGS. 2 and 3 and Table 1, 1 is surprisingly found to be an ERβ specific agonist relative to B and I.

EXAMPLE 16

Expression Profiling of Compounds 1, B and I in NSCL, Pancreas, and Ovarian Tumor Cell Lines The study includes three human tumor cell lines: A549, Panc-1, and SK-OV-3. The lines are each grown in two flasks cultured to roughly 40% confluence. One of the flasks is treated by addition of drug to the culture media at a various concentrations. The other, mock treated, flask is treated only with the vehicle used to solubilize and deliver the drug. RNA extracted from the pairs of treated and untreated samples is subjected to microarray analysis on Agilent Whole Human Genome Microarrays (G4112F). Each analysis reports the difference in abundance of messenger RNAs for each of the 41,000 specific mRNA detectors on the array. This direct comparison of the treated versus untreated samples for each cell line provides extremely sensitive detection of changes in mRNA abundance resulting from the drug treatment. As each cell line comparison is self-normalized, the results can be compared across the samples with high confidence.

Cell Preparation

Three human tumor cell lines, A549, Panc-1, and SK-OV-3, are each grown in two flasks cultured to roughly 40% confluence. One of the flasks is treated by addition of compound 1 to the culture media at concentrations according to Table 1 above. The other, mock treated, flask is treated only with the vehicle used to solubilize and deliver the drug. All flasks are cultured for a further 24 hours, and then the cells are scraped free and washed in ice-cold PBS, then collected by centrifugation. The harvested cells are immediately frozen, and stored at −80° C. or colder. It is visually noticeable that the treated cells yielded less mass than the untreated cells.

RNA Purification

Total RNA is prepared from the frozen tissue samples using Trizol-based cell lysis followed by 65° C. hot phenol extraction and RNeasy chromatography purification. The purified RNA samples are analyzed spectrophotometrically. The concentration of RNA is determined by measuring the absorbance at 260 nm (A260). Given an absorbance of 1 unit at 260 nm corresponds to 35 μg of RNA per ml when measured at pH 11.

RNA Quality Assessment—A260/A280 Absorbance Ratios

The ratio of the readings at 260 nm and 280 nm (A260/A280) provides an estimate of the purity of RNA with respect to contaminants that absorb UV, such as protein. RNA has a theoretical A260/A280 ratio (10 mM Tris-Cl, pH 7.5) of approximately 2.1. Extracted RNAs having an A260/A280 ratio of 1.8 or greater provide excellent results in this assay.

RNA Quality Assessment—Capillary Electrophoresis

The RNA is tested for relative integrity by determining the ratio of intact 28S and 18S ribosomal RNAs, using capillary electrophoresis (Agilent BioAnalyzer). Completely intact RNA has a 28S/18S ratio of 2.2. All RNAs accepted for array analysis have ratios exceeding 1, the minimal 28S/18S ratio for reliably reproducible microarray results as determined by review of internal reproducibility among samples with varying 28S/18S ratios.

Probe Production and Chip Hybridization

All RNAs are labeled using 1 microgram of RNA as input to an Agilent Low Input Labeling reaction.

Test RNA is labeled with Cy5 (650 nm emitter) and reference RNA is labeled with Cy3 (550 nm emitter) nucleotides. Labeling, hybridizations and subsequent washings are carried out on Agilent H1Av2 human expression chips. The resulting hybridized chips are scanned on an Agilent microarray scanner, and intensity information for each detector spot is extracted from the scanned image using Agilent feature extraction software. The set of data images and extracted measurements from each image are supplied.

The most telling test of the quality of the hybridization is the level of variance in reported ratios from the large number of duplicates of genes printed on these chips. A set of gene probes is each printed ten times in random positions across the array. The median value of the standard deviation of the $\log_2$ ratio across all the sets is used as an estimator of the overall standard deviation across the entire array.

Data and Analysis

The key data for all three hybridizations is collected in a FileMaker Pro relational database to allow for easy formulation of searches that can identify genes that exhibit particular transcriptional patterns. The data reported are the red (treated) and green (untreated) background-subtracted signals. This is the least modified form of the data. A background "surface" is estimated across the slide, based on numerous probes that are not complementary to human DNA. These serve as estimators of both non-specific binding of labeled cRNA to array surfaces and non-specific binding of labeled cRNA to the immobilized DNA oligomers. Using this information, local noise around each probe is estimated and this is subtracted from the signal found at the area of oligonucleotide deposition for each particular probe feature on the array (gBGSubSignal, rBGSubSignal). The ratio of signal from the RNA of the treated cell and the RNA of the untreated cell is reported both as a direct ratio and as the $\log_2$ ratio (Ratio, Log2Ratio). Ratios are determined in an iterative process that normalizes the intensities in each channel, so that a scalar is found that maximizes the similarity of intensities of the large number of genes that have nearly identical transcriptional levels, and thus should have ratios very close to 1.

After the ratios have been calculated for the normalized data, the various control and duplicate samples are analyzed to build a model of how reproducible the results are, and how this reproducibility is varies depending on signal strength and noise. With these parameters, an estimate of the likelihood that each ratio could have arisen if the red and green intensities are randomly drawn from a single process that produced the same distribution of intensities is produced. This probability is reported for each sample and is a measure of the probability that the ratio indicates a difference between the treated and untreated signal strengths (PValLogRatio). This probability can be used to threshold the results into changed and unchanged genes. In the database, a threshold of $p \leq 0.001$ is used as the cut point for significant change in mRNA abundance between the treated and untreated sample (Sig0.001). This threshold reduces the number of expected false positives to a reasonable level given the ~40,000 ratios that are being surveyed in each assay. A field that indicates significant change and the direction of the change relative to the untreated sample reduces the result of the assay to a trinary categorical; 1, up regulated relative to untreated, 0, unchanged relative to untreated and −1, down regulated relative to untreated (Tri). Using this representation, one easily constructs searches that identify genes that have changed in any single or multiple sets of experiments.

Gene impact on TREK1 and TREK2 is only observed with 1, and not with B or I (see Table 2). Specifically, gene transcription of TREK1 is up-regulated 2 to 50 fold in presence of 1, while gene transcription of TREK2 is up-regulated 8 to 50 fold in the presence of 1. TREK1 is important for the definition of temperature thresholds and temperature ranges in which excitation of nociceptor takes place and for the intensity of excitation when it occurs. Noel, J. et al., *EMBO J.* 28, 1308-1318 (2008), incorporated herein by reference. Similarly, TREK2 is important in neuropathic pain perception. Huang, D. et al., *Medical Hypothesis* 70, 618-624 (2007). As 1 is shown to be a specific agonist of ERβ and has had a significant impact on TREK1 and TREK2 transcription, the 6-substituted 13-demethyl estradiol derivatives of the invention are shown to be effective in the treatment of pain.

TABLE 1

| Compound | ERα(IC$_{50}$) | ERβ(IC$_{50}$) |
|---|---|---|
| I | 70 | 100 |
| B | 495 | 80 |
| 1 | 2250 | 21 |
| E2 | 1.9 | 1.7 |

TABLE 2

| Gene/Compound | Concentration | SKOV-3 (Log 2/p-value) | A549 (Log 2/p-value) | PANC1 (Log 2/p-value) |
|---|---|---|---|---|
| TREK1/1 | 20 μm | 1.96/ 0.0000 | 4.03/ 0.0000 | 4.78/ 0.0000 |
| TREK1/1 | 50 μm | 2.80/ 0.0000 | 4.07/ 0.0000 | 2.05/ 0.0000 |
| TREK1/1 | 100 μm | 1.97/ 0.0000 | 3.53/ 0.0000 | 3.51/ 0.0000 |
| TREK2/1 | 20 μm | 4.12/ 0.0000 | 3.79/ 0.0000 | 4.15/ 0.0000 |
| TREK2/1 | 50 μm | 5.56/ 0.0000 | 5.37/ 0.0000 | 4.20/ 0.0000 |
| TREK2/1 | 100 μm | 4.07/ 0.0000 | 3.00/ 0.0000 | 3.91/ 0.0000 |
| TREK1/B and TREK2/B | 20 μm/50 μm/ 100 μm | No Change for both at all conc. | No Change for both at all conc. | No Change for both at all conc. |

TABLE 2-continued

| Gene/Compound | Concentration | SKOV-3 (Log 2/p-value) | A549 (Log 2/p-value) | PANC1 (Log 2/p-value) |
|---|---|---|---|---|
| TREK1/I and TREK2/I | 20 μm/50 μm/ 100 μm | No Change for both at all conc. | No Change for both at all conc. | No Change for both at all conc. |

What is claimed is:

1. A method of treating pain in a host in need of such treatment, the method comprising administering to the host a therapeutically effective amount of a compound of formula:

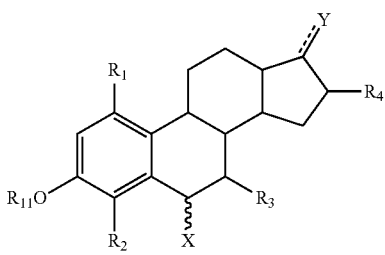

wherein $R_1$, $R_2$, $R_3$ and $R_4$ are independently selected from hydrogen, $C_1$-$C_6$ alkyl, halo, a sulfate, —OH, aryl, cycloalkyl, heteroaryl, heterocycloalkyl, —NH(CH$_2$)$_n$CH$_3$, a phosphate group, and a phosphinate group;

$R_{11}$ is selected from H, $C_1$-$C_6$ alkyl, a sulfate, —SO$_2$NH$_2$ and —NH$_2$;

X is selected from $C_1$-$C_{12}$ alkyl, $C_2$-$C_{12}$ alkenyl, $C_2$-$C_{12}$ alkynyl, halogen, —NH$_2$, —SO$_2$NH$_2$, —COOH, —CN, —CH$_2$CN, —NHCN, —CHO, —COOsalt, —OSO$_2$alkyl, —SH, —SCH$_3$, —CH[(CH$_2$)$_n$CH$_3$]COOCH$_3$, —(CH$_2$)$_m$COOCH$_3$, —(CH$_2$)$_m$—O—CH$_3$, —(CH$_2$)$_m$—O—(CH$_2$)$_n$CH$_3$, —(CH$_2$)$_m$—S—CH$_3$, —(CH$_2$)$_m$—S—(CH$_2$)$_n$CH$_3$, —(CH$_2$)$_m$—NH—(CH$_2$)$_n$CH$_3$, —C$_2$-C$_8$ alkenyl-O—(CH$_2$)$_n$CH$_3$, —C$_2$-C$_8$ alkenyl-S—(CH$_2$)$_n$CH$_3$, —C$_2$-C$_8$ alkenyl-NH—(CH$_2$)$_n$—CH$_3$, —C$_2$-C$_8$ alkynyl-NH—(CH$_2$)$_n$—CH$_3$, —C$_2$-C$_8$ alkynyl-O—(CH$_2$)$_n$—CH$_3$, —C$_2$-C$_8$ alkynyl-S—(CH$_2$)$_n$CH$_3$, —(CH$_2$)$_m$—OH, —(CH$_2$)$_m$—O—NH$_2$, —(CH$_2$)$_m$—S—NH$_2$, —NH(CH$_2$)$_m$CH$_3$, —NH(CH$_2$)$_m$OCH$_3$, —NH(CH$_2$)$_m$CHOH—COOH, —N(CH$_3$)$_2$, —(CH$_2$)$_m$(NH)CH$_2$OH, —NHCOOH, —(CH$_2$)$_m$NHCOOH, —NO$_2$, —SCN, —SO$_2$alkyl, —B(OH)$_2$, —(CH$_2$)$_m$N(CH$_3$)—SO$_2$—NH$_3$, —(CH$_2$)$_m$—NH—SO$_2$—NH$_2$, —NHC(=S)CH$_3$, and —NHNH$_2$;

Y is selected from hydrogen, =O and —OH;

m is an integer between 0-20;

n is an integer between 0-8;

the ---- symbol represents either a single or a double bond capable of forming a keto group at position 17; and the ⁓ symbol represents any type of bond regardless of the stereochemistry;

or the respective enantiomers, stereochemical isomers, tautomers or pharmaceutically acceptable salts thereof.

2. The method according to claim 1 wherein the compound is of formula:

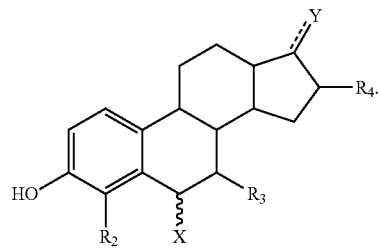

3. The method according to claim 2 wherein $R_4$ is selected from hydrogen, halo and $C_1$-$C_6$ alkyl;

$R_2$ is selected from hydrogen, —OH and halo;

$R_3$ is selected from hydrogen, halo and —OH;

X is selected from $C_1$-$C_{12}$ alkyl, $C_2$-$C_{12}$ alkenyl, —(CH$_2$)$_m$COOCH$_3$, —(CH$_2$)$_m$—O—CH$_3$, —(CH$_2$)$_m$—O—(CH$_2$)$_n$CH$_3$, —(CH$_2$)$_m$—S—CH$_3$, —(CH$_2$)$_m$—S—(CH$_2$)$_n$CH$_3$, —(CH$_2$)$_m$—NH—(CH$_2$)$_n$CH$_3$, —C$_2$-C$_8$ alkenyl-O—(CH$_2$)$_n$CH$_3$, —C$_2$-C$_8$ alkenyl-S—(CH$_2$)$_n$CH$_3$, —C$_2$-C$_8$ alkenyl-N—(CH$_2$)$_n$CH$_3$, —C$_2$-C$_8$ alkynyl-O—(CH$_2$)$_n$CH$_3$, —C$_2$-C$_8$ alkynyl-S—(CH$_2$)$_n$CH$_3$, —C$_2$-C$_8$ alkynyl-NH—(CH$_2$)$_n$—CH$_3$, —(CH$_2$)$_m$—OH, —(CH$_2$)$_m$—O—NH$_2$, —(CH$_2$)$_m$—S—NH$_2$, —NH(CH$_2$)$_m$CH$_3$, —NH(CH$_2$)$_m$OCH$_3$, —NH(CH$_2$)$_m$CHOH—COOH, —(CH$_2$)$_m$(NH)CH$_2$OH, —(CH$_2$)$_m$NHCOOH, —(CH$_2$)$_m$N(CH$_3$)—SO$_2$—NH$_3$, and —(CH$_2$)$_m$—NH—SO$_2$—NH$_2$;

m is an integer from 1-20;

n is an integer from 0-8; and the ---- symbol represents either a single or a double bond.

4. The method according to claim 3 wherein

Y is (S)-configured —OH;

$R_4$ is selected from hydrogen and $C_1$-$C_6$ alkyl;

$R_2$ and $R_3$ are hydrogen;

X is selected from $C_1$-$C_{12}$ alkyl, $C_2$-$C_{12}$ alkenyl, —(CH$_2$)$_m$—O—CH$_3$, —(CH$_2$)$_m$—O—(CH$_2$)$_n$CH$_3$, —(CH$_2$)$_m$—S—CH$_3$, and —(CH$_2$)$_m$—S—(CH$_2$)$_n$CH$_3$;

m is an integer from 1-6; and n is an integer from 0-3.

5. The method according to claim 1 where the compound is of formula:

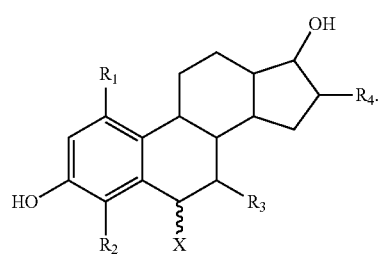

6. The method according to claim 5 wherein:

$R_1$ is selected from hydrogen, —OH and halo;

$R_4$ is selected from hydrogen, halo or $C_1$-$C_6$ alkyl;

$R_2$ is selected from hydrogen and halo;

$R_3$ is selected from hydrogen, halo and —OH;

X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, —$(CH_2)_m$—S—CH$_3$, —$(CH_2)_m$—S—$(CH_2)_n$CH$_3$, —$(CH_2)_m$—NH—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-NH—$(CH_2)_n$—CH$_3$, —$C_2$-$C_8$ alkynyl-NH—$(CH_2)_n$—CH$_3$, —$C_2$-$C_8$ alkynyl-O—$(CH_2)_n$CH$_3$, —$C_2$-$C_8$ alkynyl-S—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$N(CH$_3$)—SO$_2$—NH$_3$, and —$(CH_2)_m$—NH—SO$_2$—NH$_2$;

m is an integer from 1-20; and
n is an integer from 0-8.

7. The method according to claim 6 wherein:
$R_1$ is hydrogen;
$R_4$ is selected from hydrogen or —$C_1$-$C_6$ alkyl;
$R_2$ and $R_3$ are hydrogen;
X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, —$(CH_2)_m$—S—CH$_3$, and —$(CH_2)_m$—S—$(CH_2)_n$CH$_3$;
m is an integer from 1-12; and
n is an integer from 0-4,
wherein the C-17 hydroxyl is (S)-configured.

8. The method according to claim 1 of the formula:

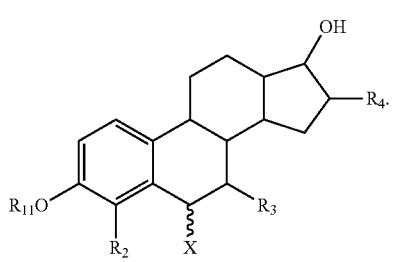

9. The method according to claim 8 wherein:
$R_{11}$ is selected from hydrogen and $C_1$-$C_6$ alkyl;
$R_4$ is selected from hydrogen, halo and $C_1$-$C_6$ alkyl;
$R_2$ is selected from hydrogen and halo;
$R_3$ is selected from hydrogen, halo and —OH;
X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, —$(CH_2)_m$—S—CH$_3$, —$(CH_2)_m$—S—$(CH_2)_n$CH$_3$, —$(CH_2)_m$—NH—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-NH—$(CH_2)_n$—CH$_3$, —$C_2$-$C_8$ alkynyl-NH—$(CH_2)_n$—CH$_3$, —$C_2$-$C_8$ alkynyl-O—$(CH_2)_n$CH$_3$, —$C_2$-$C_8$ alkynyl-S—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$N(CH$_3$)—SO$_2$—NH$_3$, and —$(CH_2)_m$—NH—SO$_2$—NH$_2$;
m is an integer from 1-20; and
n is an integer from 0-8.

10. The method according to claim 9 wherein:
$R_{11}$ is hydrogen;
$R_4$ is selected from hydrogen or $C_1$-$C_6$ alkyl;
$R_2$ and $R_3$ are hydrogen;
X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, —$(CH_2)_m$—S—CH$_3$, and —$(CH_2)_m$—S—$(CH_2)_n$CH$_3$;
m is an integer from 1-12; and
n is an integer from 0-4,
wherein the C-17 hydroxyl is (S)-configured.

11. The method according to claim 1 wherein the compound is of formula:

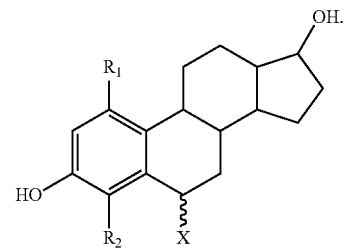

12. The method according to claim 11 wherein:
$R_1$ is selected from hydrogen, —OH and halo;
$R_2$ is selected from hydrogen and halo;
X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, —$(CH_2)_m$—S—CH$_3$, —$(CH_2)_m$—S—$(CH_2)_n$CH$_3$, —$(CH_2)_m$—NH—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-NH—$(CH_2)_n$—CH$_3$, —$C_2$-$C_8$ alkynyl-NH—$(CH_2)_n$—CH$_3$, —$C_2$-$C_8$ alkynyl-O—$(CH_2)_n$CH$_3$, —$C_2$-$C_8$ alkynyl-S—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$NHCOOH, —$(CH_2)_m$N(CH$_3$)—SO$_2$—NH$_3$, and —$(CH_2)_m$—NH—SO$_2$—NH$_2$;
m is an integer from 1-20; and
n is an integer from 0-8.

13. The method of claim 12 wherein
$R_1$ and $R_2$ are hydrogen;
X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, —$(CH_2)_m$—S—CH$_3$, and —$(CH_2)_m$—S—$(CH_2)_n$CH$_3$;
m is an integer from 1-12; and
n is an integer from 0-4,
wherein the C-17 hydroxyl is (S)-configured.

14. The method according to claim 1 wherein the compound is of formula:

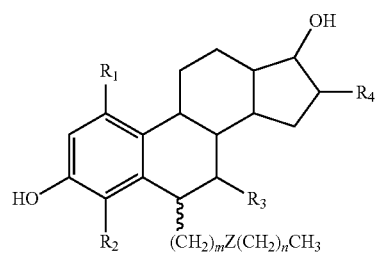

wherein Z is selected from —O—, —S— and —NH—.

15. The method of claim 14 wherein
m is 1-12;
n is 0-4;
$R_1$ is selected from hydrogen, —OH and halo;

R₄ is selected from hydrogen, halo and $C_1$-$C_6$ alkyl;
R₂ is selected from hydrogen and halo;
R₃ is selected from hydrogen, halo and —OH; and
Z is selected from —O— and —S—.

16. The method according to claim 15 wherein
m is 2-8;
n is 0-3;
R₁-R₄ are hydrogen; and
Z is —O—,
wherein the C-17 hydroxyl is (S)-configured.

17. The method according to claim 1 wherein the compound is of formula:

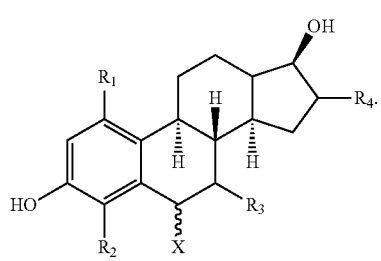

18. The method according to claim 17 wherein:
R₁ is selected from hydrogen, —OH and halo;
R₄ is selected from hydrogen, halo and $C_1$-$C_6$ alkyl
R₂ is selected from hydrogen and halo;
R₃ is selected from hydrogen, halo and —OH;
X is selected from $C_1$-$C_{12}$ alkyl, $C_2$-$C_{12}$ alkenyl, —(CH₂)$_m$COOCH₃, —(CH₂)$_m$—O—CH₃, —(CH₂)$_n$—O—(CH₂)$_n$CH₃, —(CH₂)$_m$—S—CH₃, —(CH₂)$_m$—S—(CH₂)$_n$CH₃, —(CH₂)$_m$—NH —(CH₂)$_n$CH₃, —$C_2$-$C_8$ alkenyl-O—(CH₂)$_n$CH₃, —$C_2$-$C_8$ alkenyl-S—(CH₂)$_n$CH₃, —$C_2$-$C_8$ alkenyl-NH—(CH₂)$_n$—CH₃, —$C_2$-$C_8$ alkynyl-NH—(CH₂)$_n$—CH₃, —$C_2$-$C_8$ alkynyl-O—(CH₂)$_n$CH₃, —$C_2$-$C_8$ alkynyl-S—(CH₂)$_n$CH₃, —(CH₂)$_m$—OH, —(CH₂)$_m$—O—NH₂, —(CH₂)$_m$—S—NH₂, —NH(CH₂)$_m$CH₃, NH(CH₂)$_m$OCH₃, —NH(CH₂)$_m$CHOH—COOH, —(CH₂)$_m$(NH)CH₂OH, —(CH₂)$_m$NHCOOH, —(CH₂)$_m$N(CH₃)—SO₂—NH₃, and —(CH₂)$_m$—NH—SO₂—NH₂;
m is an integer from 1-20; and
n is an integer from 0-8.

19. The method according to claim 18 wherein
R₁, R₂, R₃ and R₄ are hydrogen;
X is selected from $C_1$-$C_{12}$ alkyl, $C_2$-$C_{12}$ alkenyl, —(CH₂)$_m$—O—CH₃, —(CH₂)$_m$—O—(CH₂)$_n$CH₃, —(CH₂)$_m$—S—CH₃, and —(CH₂)$_m$—S—(CH₂)$_n$CH₃;
m is an integer from 1-12; and
n is an integer from 0-4.

20. The method according to claim 1 wherein the compound is selected from the group consisting of:
(6R,8S,9S,14S,17S)-6-(methoxymethyl)-7,8,9,11,12,13,14,15,16,17-decahydro-6H-cyclopenta[a]phenanthrene-3,17-diol;
(6R,8S,9S,14S,17S)-6-(6-methoxyhexyl)-7,8,9,11,12,13,14,15,16, 17-decahydro-6H-cyclopenta[a]phenanthrene-3,17-diol;
(6R,8S,9S,14S,17S)-6-(hydroxymethyl)-7,8,9,11,12,13,14,15,16,17-decahydro-6H-cyclopenta[a]phenanthrene-3,17-diol;
(6R,8S,9S,14S,17S)-6-((aminooxy)methyl)-7,8,9,11,12,13,14,15,16,17-decahydro-6H-cyclopenta[a]phenanthrene-3,17-diol;
(6R,8S,9S,14S,17S)-6-(((methoxymethyl)amino)methyl)-7,8,9,11,12,13,14,15,16,17-decahydro-6H-cyclopenta[a]phenanthrene-3,17-diol;
methyl (((6R,8S,9S,14S,17S)-3,17-dihydroxy-13-7,8,9,11,12,13,14,15,16,17-decahydro-6H-cyclopenta[a]phenanthren-6-yl)methyl)carbamate;
(6R,8S,9S,14S,17S)-6-methoxy-7,8,9,11,12,13,14,15,16,17-decahydro-6H-cyclopenta[a]phenanthrene-3,17-diol;
(6R,8S,9S,14S,17S)-6-(2-methoxyethyl)-7,8,9,11,12,13,14,15,16,17-decahydro-6H-cyclopenta[a]phenanthrene-3,17-diol;
(6R,8S,9S,14S,17S)-6-(4-methoxybutyl)-7,8,9,11,12,13,14,15,16,17-decahydro-6H-cyclopenta[a]phenanthrene-3,17-diol;
(6R,8S,9S,14S,17S)-6-(8-methoxyoctyl)-7,8,9,11,12,13,14,15,16,17-decahydro-6H-cyclopenta[a]phenanthrene-3,17-diol;
(6R,8S,9S,14S,17S)-3-hydroxy-6-(methoxymethyl)-7,8,9,11,12,13,14,15,16,17-decahydro-6H-cyclopenta[a]phenanthren-17-yl stearate;
(6R,8S,9S,14S,17S)-6-(4-propoxybutyl)-7,8,9,11,12,13,14,15,16,17-decahydro-6H-cyclopenta[a]phenanthrene-3,17-diol; and
(6R,8S,9S,14S,17S)-6-(5-ethoxypentyl)-7,8,9,11,12,13,14,15,16,17-decahydro-6H-cyclopenta[a]phenanthrene-3,17-diol.

21. The method of claim 1 wherein the host is a human.

22. The method according to claim 1 wherein the compound selectively binds to the ER-β receptor.

* * * * *